United States Patent [19]
Schaffer et al.

[11] Patent Number: 5,616,461
[45] Date of Patent: Apr. 1, 1997

[54] ASSAY FOR ANTIVIRAL ACTIVITY USING COMPLEX OF HERPESVIRUS ORIGIN OF REPLICATION AND CELLULAR PROTEIN

[75] Inventors: Priscilla A. Schaffer, Holliston; Christine E. Dabrowski Amaral, Plymouth, both of Mass.

[73] Assignee: Dana-Farber Cancer Institute, Boston, Mass.

[21] Appl. No.: 882,838

[22] Filed: May 14, 1992

[51] Int. Cl.$^6$ .................. C12Q 1/68; C12Q 1/70
[52] U.S. Cl. .................. 435/6; 435/5; 435/32; 436/501
[58] Field of Search .................. 435/5, 6, 7.1, 32; 935/77, 16; 436/501

[56] References Cited

U.S. PATENT DOCUMENTS

| | | | |
|---|---|---|---|
| 5,217,864 | 6/1993 | Heintz et al. | 435/6 |
| 5,223,391 | 6/1993 | Coen et al. | 435/5 |
| 5,306,619 | 4/1994 | Edwards et al. | 435/6 |
| 5,344,498 | 8/1994 | Roizman et al. | 435/5 |

FOREIGN PATENT DOCUMENTS

| | | | |
|---|---|---|---|
| WO90/06934 | 6/1990 | WIPO | C07H 15/12 |
| WO90/15884 | 12/1990 | WIPO | C12Q 1/68 |
| WO91/06626 | 5/1991 | WIPO | |
| WO91/13175 | 9/1991 | WIPO | C12Q 1/70 |

OTHER PUBLICATIONS

Rabkin, S.D. et al. 1991. Proc. Natl. Acad. Sci. USA vol. 88 pp. 10946–10950.
Bengal et al., *Cell* 68:507–519, 1992.
Bevilacqua et al., *Journal of Acquired Immune Deficiency Syndromes* 4:967–969, 1991.
Calabretta, *Cancer Research* 51:4505–4510, 1991.
Camp et al., *Journal of Virology* 65:6320–6324, 1991.
Dabrowski et al., *Journal of Virology* 65:3140–3150, 1991.
De Clercq, *Journal of Acquired Immune Deficiency Syndromes*, 4:207–218, 1991.
de Smidt et al., *Nucleic Acids Research* 19:4695–4700, 1991.
Freifeld et al., *Annu. Rev. Med.* 42:247–259, 1991.
Homann et al., *Journal of Virology* 65:1304–1309, 1991.
Horikoshi et al., *Proc. Natl. Acad. Sci. USA* 88:5124–5128, 1991.
Kaelin, Jr. et al., *Cell* 64:521–532, 1991.
Keller et al., *Nucleic Acids Research* 19:4675–4680, 1991.
Kohwi–Shigematsu et al., *Nucleic Acids Research* 19:4267–4271, 1991.
Lee et al., *Cell* 67:365–376, 1991.
Lifson et al., *Aids Research and Human Retroviruses* 7:521–527, 1991.
Meyers, *Annu. Rev. Med.* 42:179–187, 1991.
Orson et al, *Nucleic Acids Research* 19:3435–3441, 1991.
Pascal et al., *Genes & Development* 5:1646–1656, 1991.
Postel et al., *Proc. Natl. Acad. Sci. USA* 88:8227–8231, 1991.
Pardridge et al., *FEBS Letters* 288:30–32, 1991.
Phillips et al., *Journal of Acquired Immune Deficiency Syndromes* 4:959–966, 1991.
Rawlinson et al., *Nucleic Acids Research* 19:4779, 1991.
Richman, *Annu. Rev. Med.* 42:69–90, 1991.
Sock et al., *Virology* 182:298–308, 1991.
Storey et al., *Nucleic Acids Research* 19:4109–4114, 1991.
Turner et al., *Journal of Acquired Immune Deficiency Syndromes* 4:1059–1071, 1991.
Wong et al., *Journal of Virology* 65:2601–2611, 1991.
Yarchoan et al., *Blood* 78:859–884, 1991.
Buck et al., *Science* 248:208–212, 1990.

(List continued on next page.)

*Primary Examiner*—Mary E. Mosher
*Attorney, Agent, or Firm*—Panitch Schwarze Jacobs & Nadel, P.C.

[57] ABSTRACT

The invention features methods and compositions useful for identifying candidate compounds for antiviral activity, useful for inhibiting replication of a DNA virus, and useful for treating an animal infected with a DNA virus.

2 Claims, 11 Drawing Sheets

| | |
|---|---|
| SITE I | G C G T T C G C A C T T C G T C C C A A T |
| SITE II | G T G C T C G C A C T T C G C C C T A A T |
| SITE III | G C G T T C T C A C T T C T T T T A C C C |

OTHER PUBLICATIONS

Camerini–Otero et al., "Method of forming Three–Stranded DNA," Patent Application filed Nov. 9, 1990.
Huang et al., *Genes & Development* 4:287–298, 1990.
Ingraham et al., *Cell* 61:1021–1033, 1990.
Meek et al., *Nature* 343:90–92, 1991.
Rinaldo, Jr., *Annu. Rev. Med.* 41:331–338, 1990.
Shapira–Nahor et al., *Cellular Immunology* 128:101–117, 1990.
Stow et al., *Virology* 177:570–577, 1990.
Tempst et al., *Electrophoresis* 11:537, 1990.
Baumann et al., *Journal of Virology* 63:1275–1283, 1989.
Cho et al., Molecular and Cellular Biology, 9:135–143, 1989.
Maher et al., Science 245:725–730, 1989.
Loke et al., Proc. Natl. Acad. Sci. USA 86:3474–3478, 1989.
Nara et al., Proc. Natl. Acad. Sci. USA 86:7139–7143, 1989.
Olivo et al., Journal of Virology 63:196–204, 1989.
Yakubov et al., Proc. Natl. Acad. Sci. USA 86:6454–6458, 1989.
Pruijn et al., Nucleic Acids Research 17:1845–1863, 1989.
Challberg et al., Anna. Rev. Biochem. 58:671–717, 1989.
Chodosh et al., Cell 53:11–24, 1988.
Cooney et al., Science 241:456–459, 1988.
Frankel et al., Cell 55:1189–1193, 1988.
Green et al., Cell 55:1179–1188, 1988.
Hanvey et al., Proc. Natl. Acad. Sci. USA 85:6292–6296, 1988.
Koff et al., Journal of Virology 62:4096–4103, 1988.
Lifson et al., Science 241:712–716, 1988.
McClements et al., Virology 162:270–273, 1988.
McGeoch et al., J. Gen. Virol. 69:1531–1574, 1988.
McGeoch et al., J. Virology 62:444–453, 1988.
Michael et al., Science 239:1531–1534, 1988.
O'Neill et al., The Journal of Biological Chemistry 263, 931–937, 1988.
Wu et al., Journal of Virology 62:435–443, 1988.
Fechheimer et al., Proc. Natl. Acad. Sci. USA 84:8463–8467, 1987.
Jones et al., Cell, 48:79–89, 1987.
Chodosh et al., Molecular and Cellular Biology 6:4723–4733, 1986.
Cohen et al., Nature 321:441–443, 1986.
Dutia et al., Nature 321:439–441, 1986.
Lockshon et al., J. Virol. 58:513–521, 1986.
Smith et al., Proc. Natl. Acad. Sci. USA 83:2787–2791, 1986.
Stow et al., J. Gen. Virol. 67:1613–1623, 1986.
DeLuca et al., Molecular and Cellular Biology 5:1997–2008, 1985.
Spaete et al., Proc. Natl. Acad. Sci USA 82:694–698, 1985.
Weller et al., Molecular and Cellular Biology, 5:930–942, 1985.
Stow et al., Virology 130:427–438, 1983.
Weller et al., Journal of Virology 45:354–366, 1983.
Samuels et al., The Journal of Biological Chemistry 257:14419–14427, 1982.
Hager et al., Analytical Biochemistry 109:76–86, 1980.
Bradford, Analytical Biochemistry 72:248–254, 1976.
Stow, Nigel D., "Herpes Simplex Virus Type 1 Origin–Dependent DNA Replication in Insect Cells Using Recombinant Baculoviruses", *J. Gen. Virol.*, (1992) 73:313–321.

| SITE I | GCGTTCGCACTTCGTCCCAAT |
| SITE II | GTGCTCGCACTTCGCCCTAAT |
| SITE III | GCGTTCTCACTTCTTTTACCC | lane 1: no competitor
lane 2: 250X non-specific competitor
lane 3: 250X specific competitor

Probes

| | |
|---|---|
| SITE I | G C G A A G C G T T C G C A C T T C G T C C C A A T |
| 1 | G C ☐ A G C G T T C G C A C T T C G T C C C A A T |
| 2 | G C G A ☐ C G T T C G C A C T T C G T C C C A A T |
| 3 | G C G A A G ☐ T T C G C A C T T C G T C C C A A T |
| 4 | G C G A A G C ☐ T T C G C A C T T C G T C C C A A T |
| 5 | G C G A A G C G ☐ C G C A C T T C G T C C C A A T |
| 6 | G C G A A G C G T T C ☐ A C T T C G T C C C A A T |
| 7 | G C G A A G C G T T C G C ☐ T T C G T C C C A A T |
| 8 | G C G A A G C G T T C G C A C ☐ C G T C C C A A T |
| 9 | G C G A A G C G T T C G C A C T T ☐ T C C C A A T |
| 10 | G C G A A G C G T T C G C A C T T C G T C C ☐ A T |
| 11 | G C G A A G C G T T C G C A C T T C G T C C C A ☐ |
| 12 | G C G A A G C G T T A G C A C T T C G T C C C A A T |
| 13 | G C G A A G C G T T A A C A C T T C G T C C C A A T |

|  |  |  |  | AT |  |  |
|---|---|---|---|---|---|---|
| HSV-1 | oriS | site III | site I | | site II | |
| | oriL | site III | site I | | site I | site III |
| HSV-2 | oriS | site III | site I | | site II | |
| | oriL | site III | site I | | site I | site III |
| MDV | | | site I | | site I | |
| EHV-1 | | | site I | | site I | site I |
| VZV | | | site I | | | |

FIG. 10b

|  |  | SITE I | | | % homology |
|---|---|---|---|---|---|
| HSV-1 | oriS | GCGTTCGCAC | TTCGT | CCCAAT | |
| | oriL | GCGTTCGCAC | TTTGT | CCTAAT | 90 |
| | oriL | GCGTTCGCAC | TTTGT | CCTAAT | 90 |
| HSV-2 | oriS | GCGTTCGCAC | TTCGT | CCTAAT | 95 |
| | oriL | GCGTTCGCAC | TTTGT | CCTAAT | 90 |
| | oriL | GCGTTCGCAC | TTTGT | CCTAAT | 90 |
| MDV | | GCGTTCGCAC | CGCGA | ACCAAT | 81 |
| | | GCGTTCGCAC | CTTGC | GCCAAT | 81 |
| EHV-1 | | CCGTTCGCAC | CAATA | ACCAAT | 67 |
| | | GTGTTCGCAC | TTTGT | TGCAAT | 81 |
| | | GTGTTCGCAC | TTCTT | ATCCGT | 71 |
| VZV | | CCGTTCGCAC | TTTCT | TTCTAT | 71 |

SEQUENCE LISTING ( 1 ) GENERAL INFORMATION:

( i i i ) NUMBER OF SEQUENCES: 49

( 2 ) INFORMATION FOR SEQ ID NO: 1:

( i ) SEQUENCE CHARACTERISTICS:
        ( A ) LENGTH: 9
        ( B ) TYPE: nucleic acid
        ( C ) STRANDEDNESS: single
        ( D ) TOPOLOGY: linear ( x i ) SEQUENCE DESCRIPTION: SEQ ID NO: 1:

Y G T Y Y Y A A T                9

( 2 ) INFORMATION FOR SEQ ID NO: 2:

( i ) SEQUENCE CHARACTERISTICS:
        ( A ) LENGTH: 9
        ( B ) TYPE: nucleic acid
        ( C ) STRANDEDNESS: single
        ( D ) TOPOLOGY: linear ( x i ) SEQUENCE DESCRIPTION: SEQ ID NO: 2:

C G T C C C A A T                9

( 2 ) INFORMATION FOR SEQ ID NO: 3:

( i ) SEQUENCE CHARACTERISTICS:
                ( A ) LENGTH: 8
                ( B ) TYPE: nucleic acid
                ( C ) STRANDEDNESS: single
                ( D ) TOPOLOGY: linear ( x i ) SEQUENCE DESCRIPTION: SEQ ID NO: 3:

GTTCGCAC                                8

( 2 ) INFORMATION FOR SEQ ID NO: 4:

( i ) SEQUENCE CHARACTERISTICS:
                ( A ) LENGTH: 19
                ( B ) TYPE: nucleic acid
                ( C ) STRANDEDNESS: single
                ( D ) TOPOLOGY: linear ( x i ) SEQUENCE DESCRIPTION: SEQ ID NO: 4:

GTTCGCACTT CGTCCCAAT                    19

( 2 ) INFORMATION FOR SEQ ID NO: 5:

( i ) SEQUENCE CHARACTERISTICS:
                ( A ) LENGTH: 17
                ( B ) TYPE: nucleic acid
                ( C ) STRANDEDNESS: single
                ( D ) TOPOLOGY: linear ( x i ) SEQUENCE DESCRIPTION: SEQ ID NO: 5:

GTTCGCACCG TCCCAAT                      17

( 2 ) INFORMATION FOR SEQ ID NO: 6:

( i ) SEQUENCE CHARACTERISTICS:
                ( A ) LENGTH: 19
                ( B ) TYPE: nucleic acid
                ( C ) STRANDEDNESS: single
                ( D ) TOPOLOGY: linear ( x i ) SEQUENCE DESCRIPTION: SEQ ID NO: 6:

GTTAGCACTT CGTCCCAAT                    19

( 2 ) INFORMATION FOR SEQ ID NO: 7:

( i ) SEQUENCE CHARACTERISTICS:
                ( A ) LENGTH: 19
                ( B ) TYPE: nucleic acid
                ( C ) STRANDEDNESS: single
                ( D ) TOPOLOGY: linear ( x i ) SEQUENCE DESCRIPTION: SEQ ID NO: 7:

GTTAACACTT CGTCCCAAT                    19

( 2 ) INFORMATION FOR SEQ ID NO: 8:

( i ) SEQUENCE CHARACTERISTICS:
                ( A ) LENGTH: 17
                ( B ) TYPE: nucleic acid
                ( C ) STRANDEDNESS: single
                ( D ) TOPOLOGY: linear ( x i ) SEQUENCE DESCRIPTION: SEQ ID NO: 8:

GTTAGCACCG TCCCAAT                      17

( 2 ) INFORMATION FOR SEQ ID NO: 9:

( i ) SEQUENCE CHARACTERISTICS:

( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 9:

GTTAACACCG TCCCAAT         17

( 2 ) INFORMATION FOR SEQ ID NO: 10:

( i ) SEQUENCE CHARACTERISTICS:
( A ) LENGTH: 19
( B ) TYPE: nucleic acid
( C ) STRANDEDNESS: single
( D ) TOPOLOGY: linear ( x i ) SEQUENCE DESCRIPTION: SEQ ID NO: 10:

GTTCGCAC Y Y  Y GT Y Y Y AAT    19

( 2 ) INFORMATION FOR SEQ ID NO: 11:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 11:

GTTCGCAC Y G  T Y Y Y AAT    17

( 2 ) INFORMATION FOR SEQ ID NO: 12:

( i ) SEQUENCE CHARACTERISTICS:
( A ) LENGTH: 17
( B ) TYPE: nucleic acid
( C ) STRANDEDNESS: single
( D ) TOPOLOGY: linear ( x i ) SEQUENCE DESCRIPTION: SEQ ID NO: 12:

AGCGTTCGCA CTTCGTC         17

( 2 ) INFORMATION FOR SEQ ID NO: 13:

( i ) SEQUENCE CHARACTERISTICS:
( A ) LENGTH: 13
( B ) TYPE: nucleic acid
( C ) STRANDEDNESS: single
( D ) TOPOLOGY: linear ( x i ) SEQUENCE DESCRIPTION: SEQ ID NO: 13:

GGCGAAGTGC GAG         13

( 2 ) INFORMATION FOR SEQ ID NO: 14:

( i ) SEQUENCE CHARACTERISTICS:
( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 14:

AAAAGAAGTG AGAACGCG         18

( 2 ) INFORMATION FOR SEQ ID NO: 15:

( i ) SEQUENCE CHARACTERISTICS:
( A ) LENGTH: 18
( B ) TYPE: nucleic acid ( C ) STRANDEDNESS: single
( D ) TOPOLOGY: linear ( x i ) SEQUENCE DESCRIPTION: SEQ ID NO: 15:

AATATATATA TATTATTA                    18

( 2 ) INFORMATION FOR SEQ ID NO: 16:

( i ) SEQUENCE CHARACTERISTICS:
( A ) LENGTH: 26
( B ) TYPE: nucleic acid
( C ) STRANDEDNESS: single
( D ) TOPOLOGY: linear ( x i ) SEQUENCE DESCRIPTION: SEQ ID NO: 16:

GCGAAGCGTT CGCACTTCGT CCCAAT           26

( 2 ) INFORMATION FOR SEQ ID NO: 17:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 17:

GCAGCGTTCG CACTTCGTCC CAAT             24

( 2 ) INFORMATION FOR SEQ ID NO: 18:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 18:

GCGACGTTCG CACTTCGTCC CAAT             24

( 2 ) INFORMATION FOR SEQ ID NO: 19:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 19:

GCGAAGTTCG CACTTCGTCC CAAT             24

( 2 ) INFORMATION FOR SEQ ID NO: 20:

( i ) SEQUENCE CHARACTERISTICS:
( A ) LENGTH: 25
( B ) TYPE: nucleic acid
( C ) STRANDEDNESS: single
( D ) TOPOLOGY: linear ( x i ) SEQUENCE DESCRIPTION: SEQ ID NO: 20:

GCGAAGCTTC GCACTTCGTC CCAAT            25

( 2 ) INFORMATION FOR SEQ ID NO: 21:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 21:

GCGAAGCGCG CACTTCGTCC CAAT                24

( 2 ) INFORMATION FOR SEQ ID NO: 22:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 22:

GCGAAGCGTT CACTTCGTCC CAAT                24

( 2 ) INFORMATION FOR SEQ ID NO: 23:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 23:

GCGAAGCGTT CGCTTCGTCC CAAT                24

( 2 ) INFORMATION FOR SEQ ID NO: 24:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 24:

GCGAAGCGTT CGCACCGTCC CAAT                24

( 2 ) INFORMATION FOR SEQ ID NO: 25:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 25:

GCGAAGCGTT CGCACTTTCC CAAT                24

( 2 ) INFORMATION FOR SEQ ID NO: 26:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 26:

GCGAAGCGTT CGCACTTCGT CCAT                24

( 2 ) INFORMATION FOR SEQ ID NO: 27:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 27:

```
       GCGAAGCGTT CGCACTTCGT CCCA                    24
```

( 2 ) INFORMATION FOR SEQ ID NO: 28:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( x i ) SEQUENCE DESCRIPTION: SEQ ID NO: 28:

```
       GCGAAGCGTT AGCACTTCGT CCCAAT                  26
```

( 2 ) INFORMATION FOR SEQ ID NO: 29:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( x i ) SEQUENCE DESCRIPTION: SEQ ID NO: 29:

```
       GCGAAGCGTT AACACTTCGT CCCAAT                  26
```

( 2 ) INFORMATION FOR SEQ ID NO: 30:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( x i ) SEQUENCE DESCRIPTION: SEQ ID NO: 30:

```
       GTTCGCACNN CGTCCCAAT                          19
```

( 2 ) INFORMATION FOR SEQ ID NO: 31:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( x i ) SEQUENCE DESCRIPTION: SEQ ID NO: 31:

```
       TTGGMNNNN NGCCAAN                             16
```

( 2 ) INFORMATION FOR SEQ ID NO: 32:

( i ) SEQUENCE CHARACTERISTICS:
    ( A ) LENGTH: 14
    ( B ) TYPE: nucleic acid
    ( C ) STRANDEDNESS: single
    ( D ) TOPOLOGY: linear ( x i ) SEQUENCE DESCRIPTION: SEQ ID NO: 32:

```
       Y AG Y NNNRRC CAAT                            14
```

( 2 ) INFORMATION FOR SEQ ID NO: 33:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( x i ) SEQUENCE DESCRIPTION: SEQ ID NO: 33:

```
       GCGTTCGCAC TTCGTCCCAA T                       21
```

( 2 ) INFORMATION FOR SEQ ID NO: 34:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 34:

GCGTTCGCAC TTTGTCCTAA T        21

( 2 ) INFORMATION FOR SEQ ID NO: 35:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 35:

GCGTTCGCAC TTTGTCCTAA T        21

( 2 ) INFORMATION FOR SEQ ID NO: 36:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 36:

GCGTTCGCAC TTCGTCCTAA T        21

( 2 ) INFORMATION FOR SEQ ID NO: 37:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 37:

GCGTTCGCAC TTTGTCCTAA T        21

( 2 ) INFORMATION FOR SEQ ID NO: 38:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 38:

GCGTTCGCAC TTTGTCCTAA T        21

( 2 ) INFORMATION FOR SEQ ID NO: 39:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 39:

GCGTTCGCAC CGCGAACCAA T        21

( 2 ) INFORMATION FOR SEQ ID NO:40:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 40:

GCGTTCGCAC CTTGCGCCAA T          21

( 2 ) INFORMATION FOR SEQ ID NO: 41:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 41:

CCGTTCGCAC CAATAACCAA T          21

( 2 ) INFORMATION FOR SEQ ID NO: 42:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 42:

GTGTTCGCAC TTTGTTGCAA T          21

( 2 ) INFORMATION FOR SEQ ID NO: 43:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 43:

GTGTTCGCAC TTCTTATCCG T          21

( 2 ) INFORMATION FOR SEQ ID NO: 44:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 44:

CCGTTCGCAC TTTCTTTCTA T          21

( 2 ) INFORMATION FOR SEQ ID NO: 45:

( i ) SEQUENCE CHARACTERISTICS:
        ( A ) LENGTH: 76
        ( B ) TYPE: nucleic acid
        ( C ) STRANDEDNESS: single
        ( D ) TOPOLOGY: linear ( x i ) SEQUENCE DESCRIPTION: SEQ ID NO: 45:

TAAAAGAAGT GAGAACGCGA AGCGTTCGCA CTTCGTCCCA ATATATATAT ATTATTAGGG    60

CGAAGTGCGA GCACTG          76

( 2 ) INFORMATION FOR SEQ ID NO: 46:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 46:

ACTAGTTAAT TAACTAGT                18

( 2 ) INFORMATION FOR SEQ ID NO: 47:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 47:

AGCTTCATGG AATGCAGCCA AACCATGG        28

( 2 ) INFORMATION FOR SEQ ID NO: 48:

( i ) SEQUENCE CHARACTERISTICS:
        ( A ) LENGTH: 32
        ( B ) TYPE: nucleic acid
        ( C ) STRANDEDNESS: single
        ( D ) TOPOLOGY: linear ( x i ) SEQUENCE DESCRIPTION: SEQ ID NO: 48:

GATCTGCGAA GCGGTGATCG CGCCACCCAA TG      32

( 2 ) INFORMATION FOR SEQ ID NO: 49:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 49:

GTTCGCACTT CGTCCCAAT              19

ASSAY FOR ANTIVIRAL ACTIVITY USING COMPLEX OF HERPESVIRUS ORIGIN OF REPLICATION AND CELLULAR PROTEIN

This invention was made with Government support, and the U.S. Government therefore has certain rights in the invention.

BACKGROUND OF THE INVENTION

The field of the invention is inhibition of virus replication.

Viruses are simple forms of replicating obligate intracellular parasites that are important animal (including human) pathogens. Viruses are classified into families according to their structure and genetic composition and thus comprise two major groups, DNA and RNA viruses. DNA virus families include the Poxviruses, Herpesviruses, Adenoviruses, Papovaviruses, Parvoviruses and Hepadnaviruses.

Herpes simplex virus type 1 (HSV-1) is a member of the herpesvirus family. A ubiquitous property of the herpesviruses is their capacity to remain latent in the host in which they multiply.

HSV-1 contains a linear double-stranded DNA genome 152 kilobases in length which encodes more than 72 gene products (McGeoch et al., 1988, J. Gen. Virol. 69:1531). The products of seven viral genes are required for origin-dependent replication of the viral genome (McGneoch et al., 1988, J. Virol. 62:444; Olivo et al., 1989, J. Virol. 63:196; Wu et al., 1988, J. Virol. 62:435). These seven viral genes include the origin binding protein (OBP), the single-stranded DNA binding protein (ICP8), the viral DNA polymerase, the polymerase accessory protein, and three proteins comprising a helicase-primase complex (Challberg et al., 1989, Ann. Rev. Biochem. 58:671). Although necessary, these proteins are not sufficient for origin-dependent DNA synthesis outside the cellular milieu.

The HSV-1 genome contains two covalently linked segments termed the unique long ($U_L$) and unique short ($U_S$) segments. Each segment is flanked by inverted repeat sequences, the internal (IR) and terminal (TR) repeats. The genome contains three origins of DNA replication, one located within $U_L$ (oriL) and two within the repeat sequences flanking $U_S$ (oriS) (Challberg et al., 1989, Ann. Rev. Biochem. 58:671; Spaete et al., 1985, Proc. Natl. Acad. Sci. USA 82:694; Stow et al., Virology 130:427).

SUMMARY OF THE INVENTION

The invention features methods for identifying compounds that are useful in the treatment of vital infections and assays and kits which can be used to identify such compounds. The invention also features novel compositions and methods useful for the treatment of viral infections in animals.

The compositions and methods of the invention are based on the identification of a cellular protein which associates both with specific DNA sequences within the origin of HSV-1 DNA replication and with a viral origin-specific DNA binding protein. Viral proteins, in particular so-called "origin binding proteins", are known in the art to bind to origin specific sequences, with the result of promoting DNA replication. Cellular protein(s) which are associated with the process of viral DNA replication are the subject of the instant invention.

In one aspect, the invention features a method for screening candidate compounds for antiviral activity. The method involves combining, in the presence or absence of a candidate compound, (1) an origin binding protein of a DNA virus with (2) a DNA to which this protein binds, and (3) a cellular protein capable of binding to this DNA, wherein the cellular protein is required for replication of the DNA virus but is not a DNA polymerase; and determining whether the level of tripartite complex formation by the origin binding protein, the cellular protein and the DNA is lower in the presence of the candidate compound than in the absence of the candidate compound, a lower level in the presence of the candidate compound being an indication that the candidate compound possesses antiviral activity.

The invention also features a second method of screening candidate compounds for antiviral activity. The method involves combining, in the presence or absence of a candidate compound, an origin binding protein of a DNA virus and a cellular protein with which the origin binding protein interacts and which is necessary for the replication of the DNA virus, the cellular protein being other than a DNA polymerase, and determining whether the level of complex formation between the two proteins is lower in the presence of the candidate compound than in the absence of the candidate compound, a lower level in the presence of the candidate compound being an indication that the candidate compound possesses antiviral activity.

Another method of the invention involves screening candidate compounds for antiviral activity by combining, in the presence or absence of a candidate compound, (1) a cellular protein which binds to an origin of replication of a DNA virus and is required for viral DNA synthesis, (2) a DNA to which the cellular protein binds, provided that the cellular protein is not a DNA polymerase; and determining whether the level of complex formation by the cellular protein and the DNA is lower in the presence of the candidate compound than in the absence of the candidate compound, a lower level in the presence of the candidate compound being an indication that the candidate compound possesses antiviral activity.

The virus encoding the origin binding protein of the invention and which contains an origin of replication is preferably a Poxvirus, a Herpesvirus, an Adenovirus, a Papovavirus, a Parvovirus or a Hepadnavirus. The virus is more preferably herpes simplex virus type 1, herpes simplex virus type 2, varicella zoster virus, equine herpes virus type 1 or Marek's disease virus, and most preferably is herpes simplex virus type 1. The origin binding protein is preferably the herpes simplex virus type 1 origin binding protein (OBP) and the cellular protein is preferably OF-I as defined below.

Another feature of the invention is an antiviral composition which prevents binding of a cellular protein to a specific site on an origin of replication on the genome of a DNA virus, wherein the binding of the cellular protein to the origin is required for replication of the virus.

The invention also features an antiviral composition which prevents binding of a cellular protein to a specific site on an origin of replication on the genome of a DNA virus, wherein binding at that site is essential for replication of the virus.

The invention also features an antiviral composition which prevents the interaction of a cellular protein with an origin binding protein of a DNA virus, the interaction being essential for the replication of the virus.

The antiviral composition of the invention may be either a peptide, or a compound which is not a peptide, termed a nonpeptide (e.g., an oligodeoxyribonucleotide).

It is preferably an oligodeoxyribonucleotide comprising a first portion, which first portion has at least 70% homology (i.e., sequence identity) and preferably at least 90% homology to the sequence 5' PyGTPyPyPyAAT 3' [SEQ ID NO:1]. Most preferably, the first portion comprises the sequence 5' CGTCCCAAT 3' [SEQ ID NO:2]. The oligodeoxyribonucleotide may further comprise a second portion having at least 70% homology to the sequence 5' GTTCGCAC 3' [SEQ ID NO:3], and more preferably, having at least 90% homology to the sequence 5' GTTCGCAC 3', this second portion being 5' to the first portion. Most preferably, the oligodeoxyribonucleotide of the invention contains one of the following sequences: 5' GTTCGCACTTCGTCCCAAT 3' [SEQ ID NO:4], 5' GTTCGCACCGTCCCAAT 3' [SEQ ID NO:5], 5' GTTAGCACTTCGTCCCAAT 3' [SEQ ID NO:6], 5' GTTAACACTTCGTCCCAAT 3' [SEQ ID NO:7], 5' GTTAGCACCGTCCCAAT 3' [SEQ ID NO:8], 5' GTTAACACCGTCCCAAT 3' [SEQ ID NO:9], 5' GTTCG-CACPyPyPyGTPPyPyPyAAT 3' [SEQ ID NO:10], or 5' GTTCGCACPyGTPyPyPyAAT 3' [SEQ ID NO:11].

Origin binding protein, as used herein, is a virus-encoded protein capable of binding to a specific sequence contained within an origin of viral DNA replication. A origin of DNA replication is defined as the sequence of DNA at which DNA replication begins.

OF-I, as used herein, is a cellular protein produced by any species, which protein is not a DNA polymerase, but is capable of interacting with (1) a HSV-1 origin of DNA replication, and (2) the HSV-1 origin binding protein and is necessary for replication of the HSV-1 genome.

The antiviral composition of the invention may alternatively be a peptide which preferably comprises an amino acid sequence homologous (i.e., substantially identical) to a portion of the cellular protein described herein. The peptide may be homologous to a portion of the cellular protein (preferably OF-I) that interacts with the origin binding protein, or is homologous to a portion of the cellular protein which interacts with a DNA sequence in an origin of replication of the virus. The peptide may alternatively be homologous to a portion of a viral origin binding protein, preferably the HSV-1 origin binding protein (OBP), which portion interacts with the cellular protein OF-I.

The antiviral composition of the invention may alternatively be an antibody, such as an antibody directed against an origin binding domain of a cellular protein, such as OF-I, capable of interacting with a viral origin of replication, or an antibody directed against a domain on a viral origin binding protein, wherein the domain interacts with a cellular protein capable of binding to a viral origin of DNA replication.

The invention also features a method of inhibiting replication of a DNA virus, wherein the method involves introducing into a cell infected with the virus an antiviral composition which prevents binding of a cellular protein to a specific site on an origin of replication on the genome of a DNA virus, wherein binding at that site is essential for replication of the virus. The antiviral composition utilized in the method is, for example, one which prevents the interaction of a cellular protein with an origin binding protein of a DNA virus, wherein the interaction is essential for the replication of the virus.

The invention also features a method of treating an animal infected with a DNA virus with the antiviral composition of the invention, and a therapeutic composition comprising the antiviral composition of the invention in a pharmaceutically acceptable carrier.

The invention features a substantially pure preparation of OF-I. A substantially pure preparation of OF-I is one which is at least 50% free of other proteins with which OF-I naturally occurs within a cell. Such a preparation may be obtained, for example, by extraction from a natural source, by expression of a recombinant nucleic acid encoding OF-I, or by chemically synthesizing the OF-I, and is preferably at least 75% pure OF-I.

Another feature of the invention is an isolated DNA which encodes OF-I. Isolated DNA denotes a DNA that is free of the genes which, in the naturally-occurring genome of the organism from which the DNA of the invention is derived, flank the gene encoding OF-I. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

The invention also includes a vector (i.e., a phage a plasmid or a eukaryotic DNA virus) comprising the isolated DNA encoding OF-I, wherein the vector is capable of directing the expression of the DNA.

The invention further features a cell which contains an isolated DNA encoding OF-I, and an antibody which preferentially binds to OF-I, i.e., which forms an immune complex with OF-I.

DETAILED DESCRIPTION

The drawings are first described.

Figures 1A, 1B, 2A:
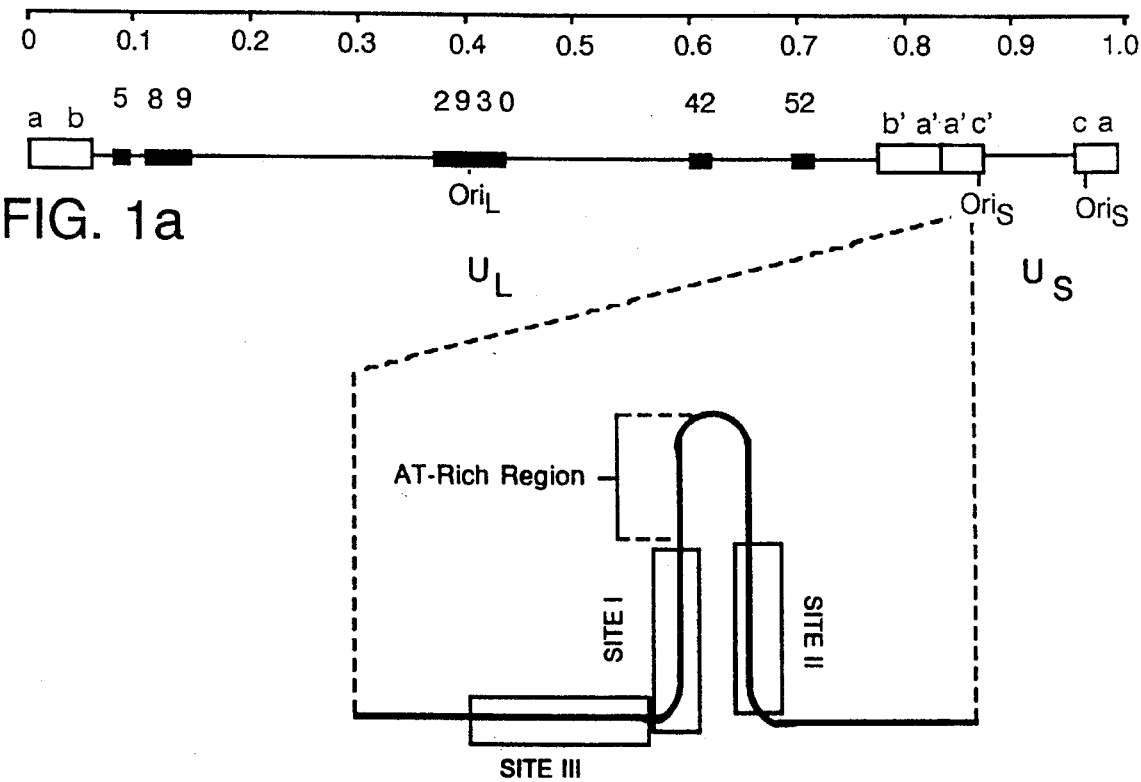

FIG. 1 is a diagram of the HSV-1 genome and oriS. FIG. 1A indicates the locations of the three origins of DNA replication and the locations of the seven essential DNA replication genes (hatched boxes). The HSV-1 genome divided into approximate map units is also shown. FIG. 1B is a diagram of oriS indicating the location of the AT-rich region and the positions of sites I, II, and III (boxes). The DNA sequence of oriS sites I, II, III, and the AT-rich region ([SEQ. ID. NOS 12, 13, 14 and 15], respectively) is also shown.

FIG. 2 is an illustration of the DNA sequences of oriS sites I, II, and III [SEQ ID NOS:12, 13, 14 and 15]. Nucleotides which have been altered compared to those present in site I DNA are shown in bold letters. FIG. 2 also contains an autoradiogram which features the relative mobilities of DNA-protein complexes formed with site I (lane 1), II (lane 2), and III (lane 3) DNA.

FIG. 3 is a demonstration of competition analysis with homologous site I, II and III DNA. Cell extracts were incubated with site I, site II, and site III probes in the presence of increasing amounts of cold homologous DNA, or a 100-fold excess of non-specific (ns) DNA as competitor. (A) Gel-shift showing competition of complexes M and M'; complex M" cannot be seen in this gel because it has the same mobility as the non-specific probe. (B) Graph of the interpolated densitometric quantitation of competition analysis of the M-like complexes. Each band was scanned with an LKB Ultrascan densitometer and compared (as a percentage) to no competitor (100%). Each value represents the average of 4 to 20 experiments.

Figure 3A:
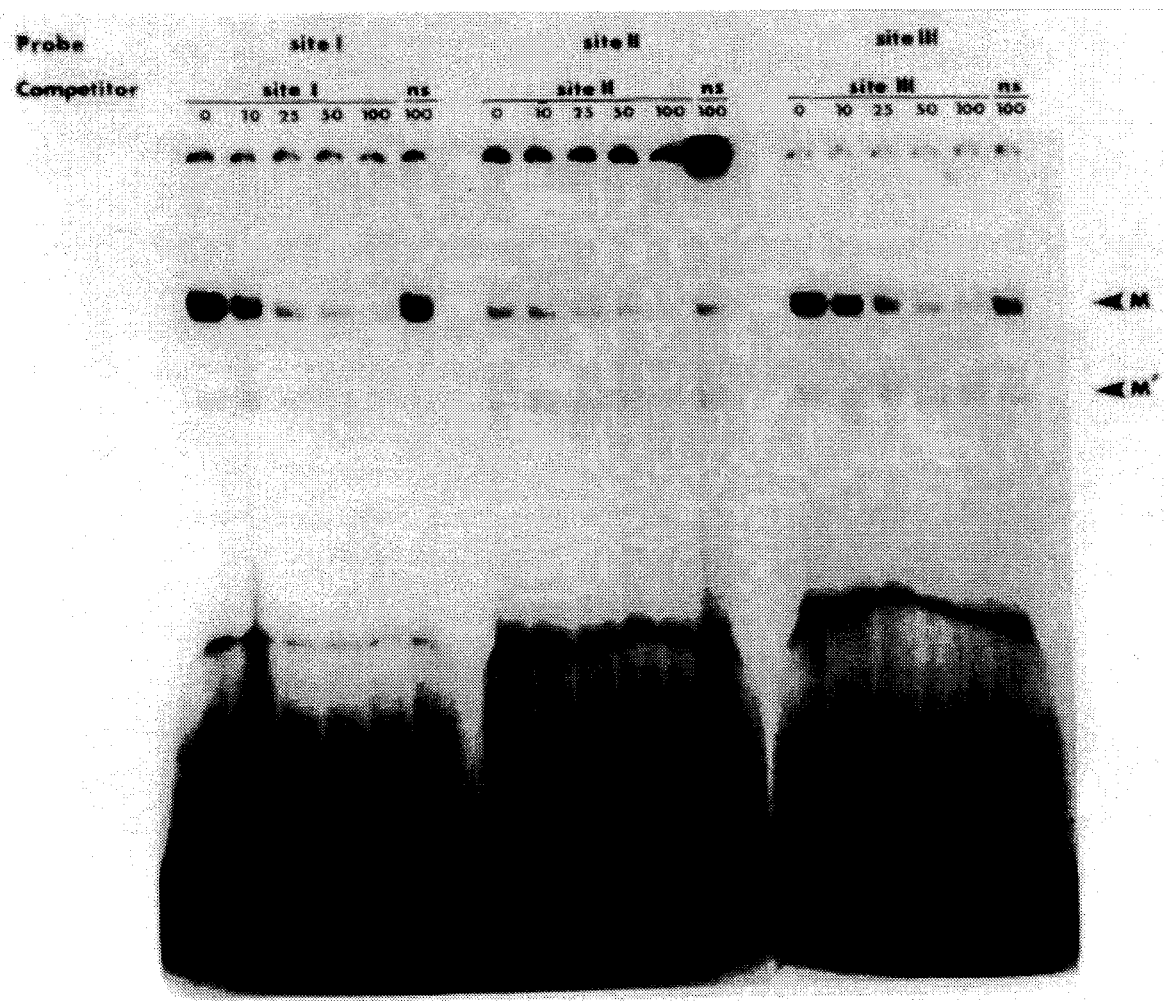
Figure 3B:
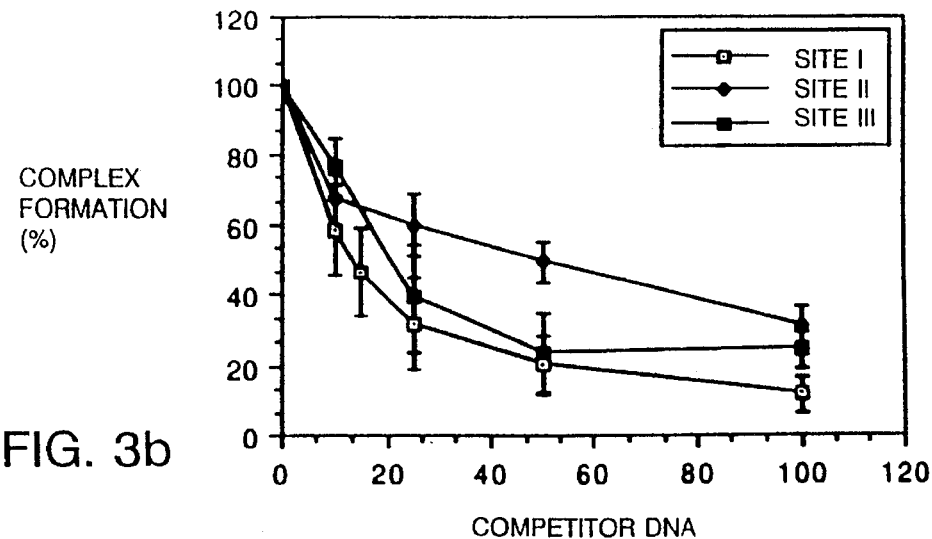
Figure 4:
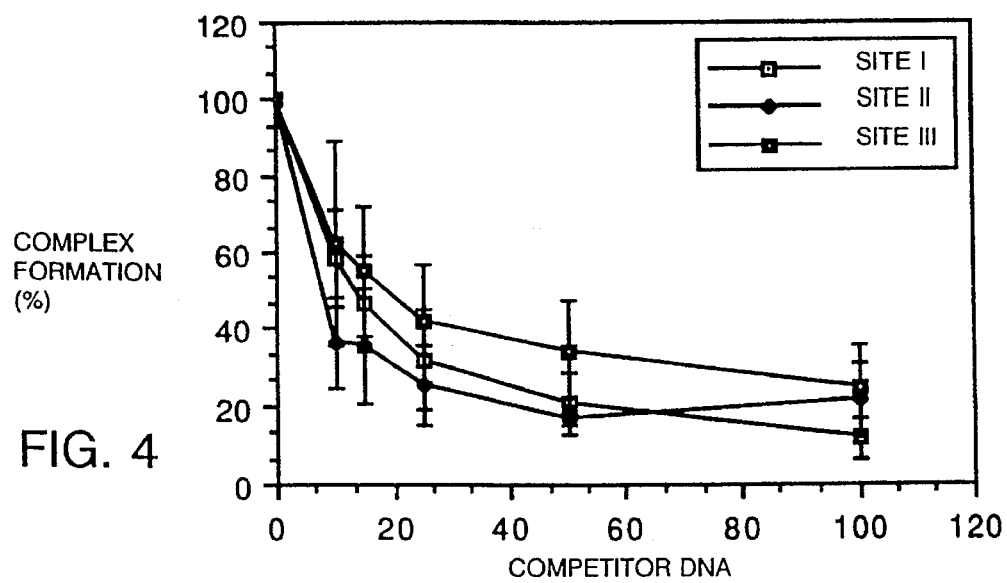

FIG. 4 is a demonstration of competition analysis with site I DNA. Cell extracts were incubated with site I, site II, and site III probes in the presence of increasing amounts of cold site I DNA as competitor. The values for the graph showing competition for formation of the M-like complexes were determined as described for FIG. 3. The values represent the average of 3 to 20 experiments.

Figure 5:
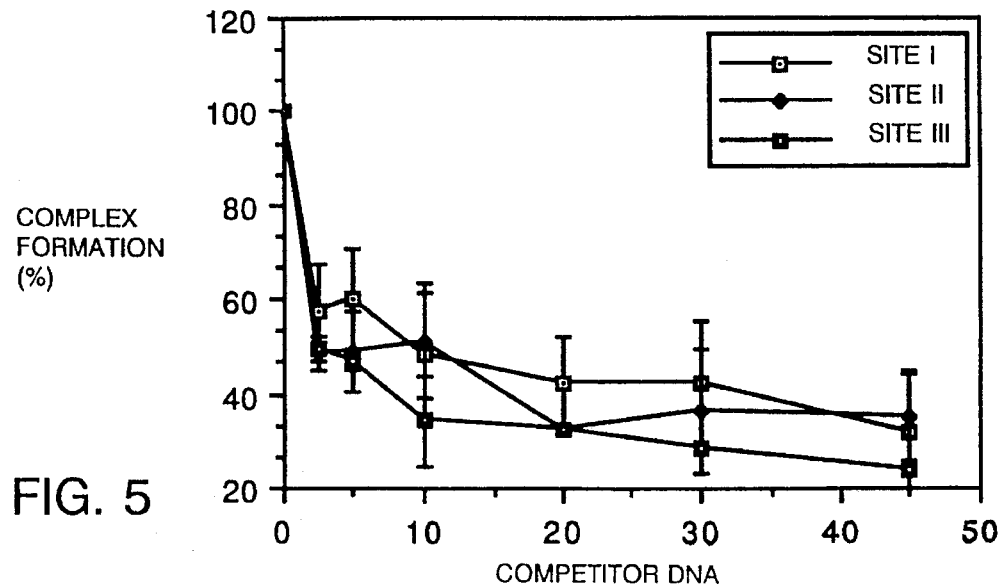

FIG. 5 is a demonstration of dissociation rate analysis. Cell extracts were incubated with the site I, site II, and site III probes. Following the initial 30 minute incubation, a 50-fold excess of cold homologous DNA was added as a competitor, and incubation was continued for the times indicated prior to electrophoresis. The values for the graph showing dissociation rates were determined as described for FIG. 3. The values represent the average of 3 to 5 experiments.

Figure 6:
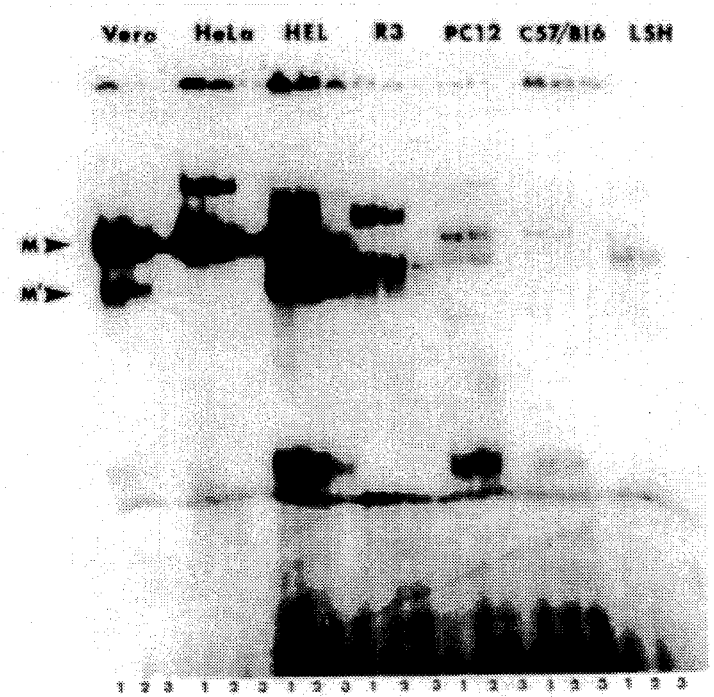

FIG. 6 demonstrates complex formation with cell extracts from animals of different species. Cell extracts from Vero (monkey), HeLa (human), HEL (human), R3 (rabbit), PC12 (rat), C57/B16 (mouse), and LSH (hamster) cells were incubated with radiolabeled site I DNA (lanes 1) in the presence of a 250-fold excess of non-specific (lanes 2) or specific site I (lanes 3) competitor DNA.

FIG. 7 is an illustration of the nucleotide sequences of site I probes. The nucleotide sequences of the wild type and mutant site I probes (1 through 13) are shown in the 5' to 3' orientation (SEQ. ID. NOS. 16, 17, 18, 19, 20, 21, 22, 23, 24, 25, 26, 27, 28, and 29, respectively).

Deleted nucleotides are indicated by open boxes; nucleotide substitutions are indicated in bold letters.

Figure 8A:
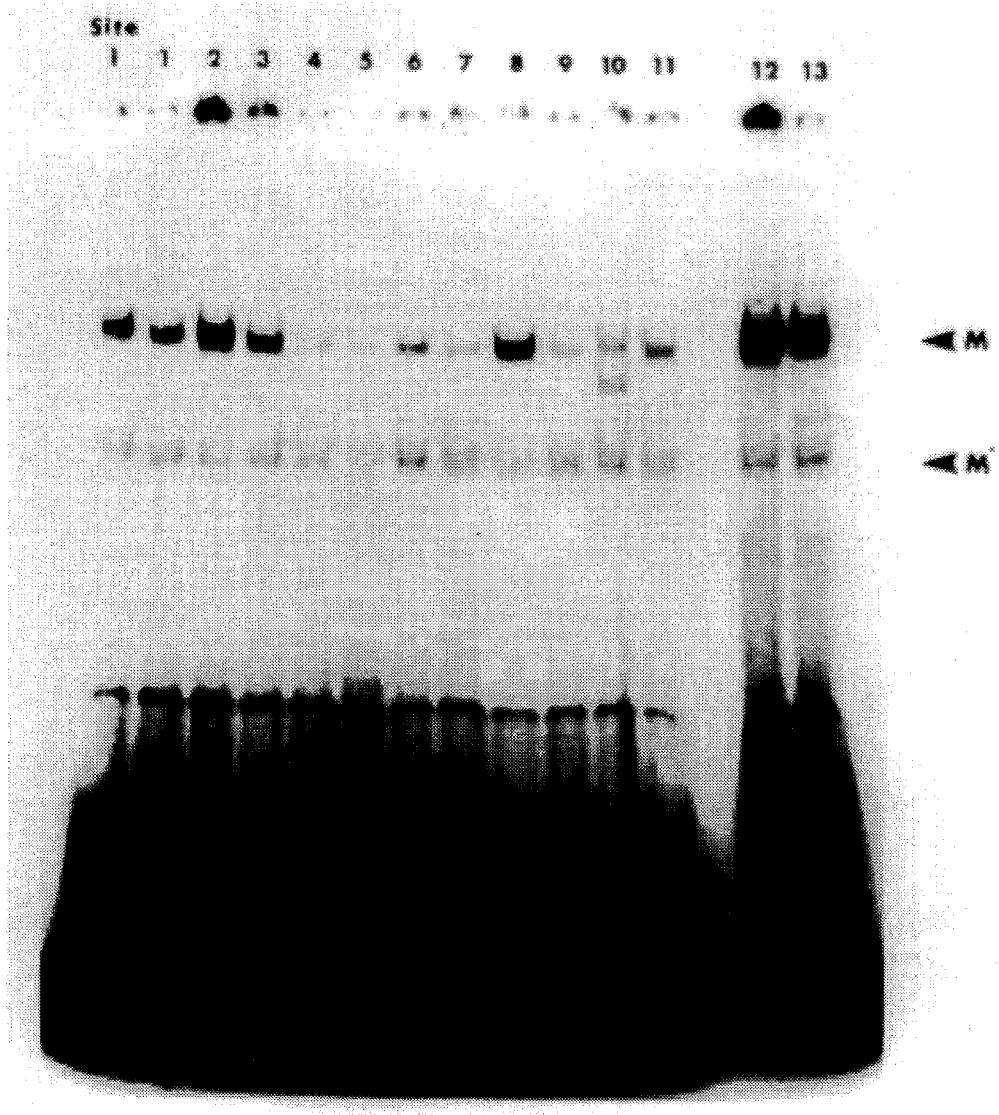
Figure 8B:
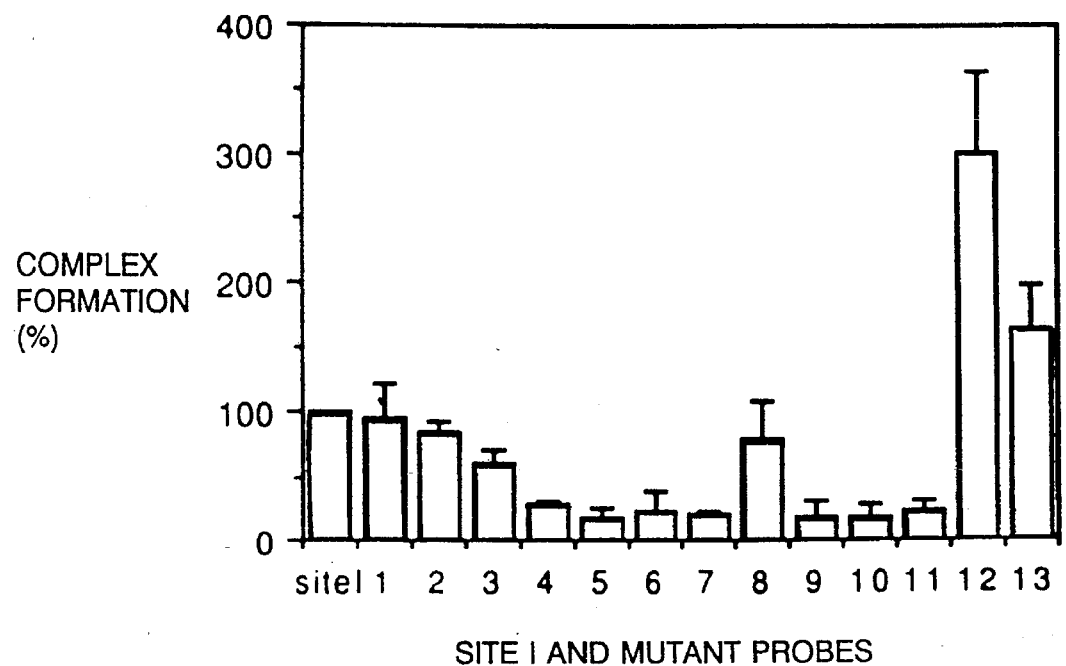

FIG. 8 demonstrates complex formation with wild type and mutant site I probes (1 through 13). (A) Gel-shift showing formation of complexes M and M'. (B) The values for the graph of M complex formation with wild type (100%) and mutant probes were determined as described for FIG. 3, and represent the average of 4 to 8 experiments.

FIG. 9 demonstrates competition and complex formation with NF-I and CP2 binding sites. (A) is the nucleotide sequence of the consensus binding sites of OF-I, NF-I and CP2 (SEQ. ID. NOS. 30, 31, and 32), and the components of the sites are shown in the boxes. Non-homologous nucleotides are in bold type. (B, left) demonstrates complexes formed when cell extracts were incubated with the site I probe and competed with cold site I, NF-I or CP2 DNA as shown in (A). Complexes formed with the site I probe were competed with increasing amounts (0-200-fold excess) of cold site I, CP2 or NF-I competitor DNA as indicated. (B, right) demonstrates complexes formed when cell extracts were incubated with site I, NF-I or CP2 probes.

FIG. 10 is a comparison of the origins of replication of five herpesviruses. (A) Comparison of the structures of the origins of replication of five herpesviruses with respect to sequences homologous to site I, II and III DNAs. (B) The nucleotide sequences homologous to site I DNA of HSV-1 oriS are compared among HSV-1 [SEQ ID NOS:33, 34, and 35] (Stow et al., 1983, Virology 130:427), HSV-2 [SEQ ID NOS:36, 37, and 38] (Lockshon et al., 1986, J. Virol. 58:513), MDV [SEQ ID NOS:39 and 40] (Camp et al., 1991, J. Virol. 65:6320), EHV-1 [SEQ ID NOS:41, 42 and 43] (Baumann et al., 1989, J. Virol. 63:1275) and VZV [SEQ IS NO:44] (Stow et al., 1986, J. Gen. Virol. 67:1613); identical nucleotides are boxed. The locations of the site I DNAs are shown above in (A).

Figure 11:
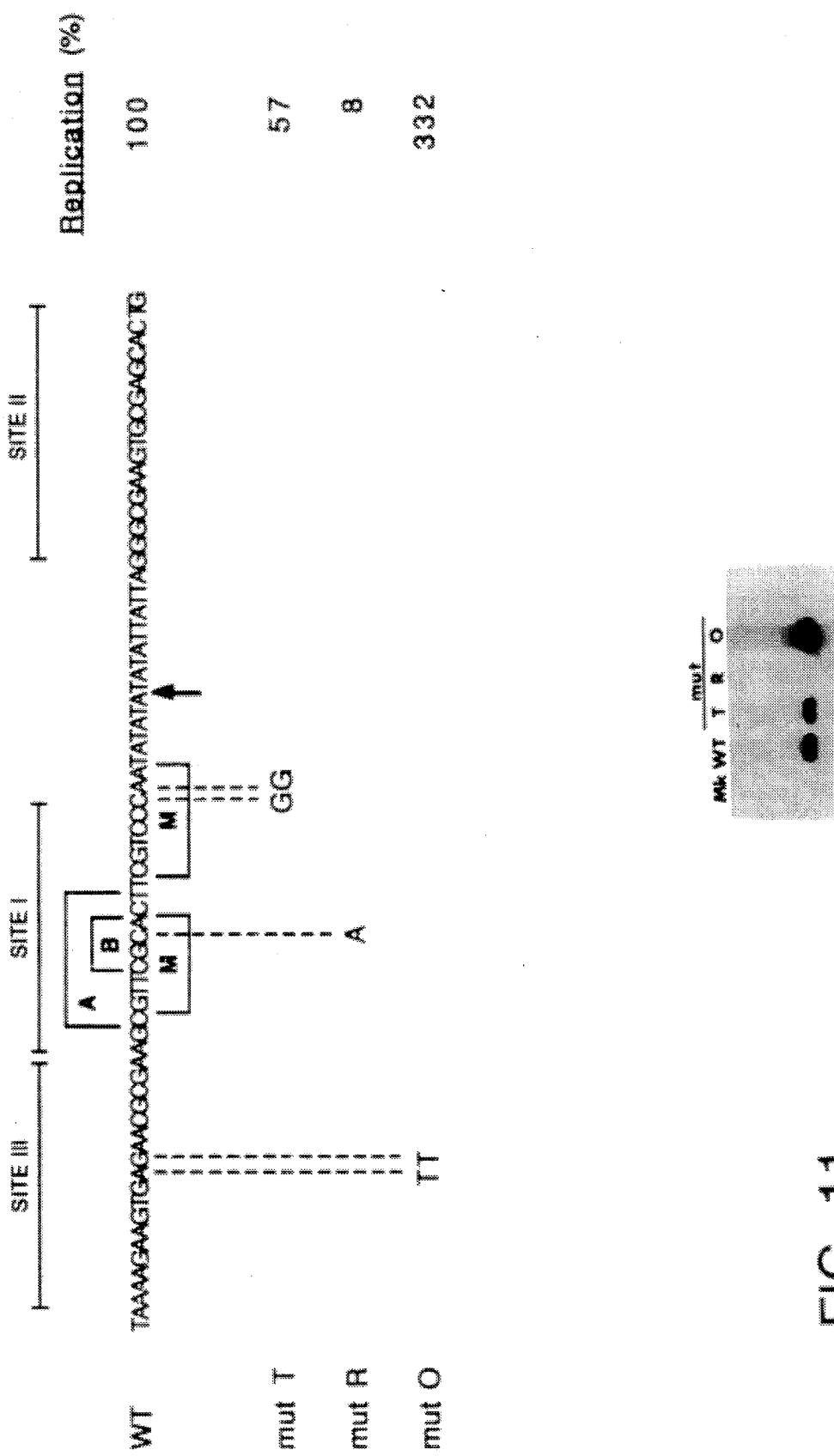

FIG. 11 demonstrates the effect of mutations in the protein binding sites in the HSV-1 origin of replication on DNA replication [SEQ ID NO:45].

The present invention provides novel methods and compositions for the treatment of viral infections of animals and for screening for such therapeutic compositions. Promising targets for antiviral therapy include viral DNA sequences that specify an origin of DNA replication, and the proteins that bind to such sequences. The examples given below relate to, but are not necessarily limited to, treatment of HSV-1 infections. It is believed that all viral DNA genomes contain at least one origin of DNA replication, and the process of DNA replication, which is essential for virus replication, requires binding of sequence-specific DNA binding proteins to that origin.

The oriS sequence of HSV-1 comprises a 90 bp sequence within which three regions sharing homology with each other, site I, site II and site III, are defined. The oriL sequence of HSV-1 also contains sites I and III DNA which are nearly identical to those of oriS. The 90 bp sequence of oriS includes a 45 bp palindromic region, which is highly homologous to the palindromic region of the larger 144 bp oriL (Stow et al., 1983, Virology 130:427; Weller et al., 1985, Mol. Cell. Biol. 5:930). An 11 bp sequence located within the palindromic region is conserved in oriS and oriL of HSV-1 and HSV-2 as well as in the oriS equivalent of a third member of the neurotropic alphaherpesviruses, varicella-zoster virus (VZV) (Stow et al., 1986, J. Gen. Virol. 67:1613). Nine to ten bp of the 11 bp sequence are conserved in the oriS equivalent of equine herpesvirus type 1 (EHV-1) and Marek's disease virus (MDV) (Bauman et al., 1989, J. Virol. 63:1275; Camp et al., 1991, J. Virol. 65:6320).

Site I, containing the 11 bp sequence is present in one copy in oriS of HSV-1 and in two copies in oriL of HSV-1, and is a high affinity binding site for the HSV-1 specified origin-specific DNA binding protein, OBP (Dabrowski et al., 1991, J. Virol. 65:3140, herein incorporated by reference). Sites II and III of HSV-1 also contain binding sites for the HSV-1 OBP (Dabrowski et al., Supra). Incubation of HSV-1 infected cell extracts with an oligonucleotide comprising either site I or site II from oriS results in the formation of two discrete OBP-containing complexes, A and B, while incubation with site III from oriS results only in the formation of complex B (Dabrowski et al., Supra).

The data presented below demonstrate the discovery that a specific protein-DNA complex, termed complex M, forms following incubation of uninfected cell extracts with HSV-1 oriS site I, II, or III DNA. The experiments reported herein establish that this complex includes a cellular protein which appears to play a crucial role in the origin-directed DNA replication of HSV-1, and by implication, other DNA viruses as well.

MATERIALS AND METHODS

Cells and virus.

Vero, HeLa, HEL, R3, LSH and C57/B16 were grown and maintained as described (Weller et al., 1983, J. Virol. 45:354). PC12 cells were grown and maintained according to the method of Cho et al. (1989, Mol. Cell. Biol. 9:135). Stocks of the HSV-1 wild-type virus, strain KOS, were grown and assayed as described by DeLuca et al. (1985, Mol. Cell. Biol. 5:1997).

Oligonucleotides and probes.

The site I, II, III, mutant site I and NS-A oligonucleotides and oligonucleotides comprising the NF-I and CP2 binding sites were synthesized in an oligonucleotide synthesizer. Complementary oligonucleotides, containing 4-bp overhangs that comprise BamHI or BglII sites, were annealed and radiolabeled using standard techniques. One strand of each oligonucleotide pair used in these experiments is shown in the 5' to 3' orientation in FIGS. 2 and 7. One strand of the non-specific competitor DNA NS-A, and DNA probes containing the consensus binding sites for transcription factor NF-I (Jones et al., 1987, Cell 48:79) or CP2 (−81 to −68) in H-2K$^b$ (Chodosh et al., 1988, Cell 53:11) is shown below, in the 5'-to-3' orientation:

NS-A: ACTAGTTAATTAACTAGT  [SEQ ID NO:46]

NF-I: AGCTTCATGGAATGCAGCCAAACC-ATGG  [SEQ ID NO:47]

CP2 (H-2K$^b$): GATCTGCGAAGCGGTGATCGCGCCAC-CCAATG  [SEQ ID NO:48]

Preparation of cell extracts and source of partially purified OBP.

One-hundred-millimeter petri dishes were seeded at a density of 2.5×10$^6$ Vero cells per dish. Cells were infected 1 day postseeding with HSV-1 (KOS) at a multiplicity of 10 plaque forming units (PFU) per cell and harvested 15 to 18 h postinfection. Uninfected cells were harvested 48 to 72 h postseeding to obtain enhanced levels of cellular proteins. Cells were harvested by scraping into the medium and pelleted at 2,000 rpm, 4° C. for 5 min. The cell pellet was rinsed once with 5 ml of phosphate-buffered saline (PBS) and repelleted. The pellet was resuspended in 0.5 ml of PBS, repelleted, and resuspended in 100 µl of NET buffer (50 mM Tris-HCl[pH 7.8], 100 mM NaCl, 1 mM EDTA), with or without 1 mM N-α-p-tosyl-L-lysine chloromethyl ketone (TLCK). The cell suspension was stored at −70° C. overnight, thawed at 37° C., and sonicated for 1 min in two 30 second bursts. Samples were pelleted at 4° C. for 10 min, and the supernatant fluid was aliquoted and stored at −70° C. Protein concentrations were determined for each sample by the method of Bradford (Bradford, 1976, Anal. Biochem. 72:248), using a standard curve generated with bovine serum albumin (BSA) as the protein source.

DNA-binding assays.

Uninfected cell extracts (10 µg protein or as noted below), or HSV-1 infected cell extracts (2 µg protein or as noted below) were incubated at 25° C. for 30 minutes with 3 to 5×10$^4$ cpm of probe (1 to 2 ng) and 1.5 µg of poly(dI-dC).poly(dI-dC) (Pharmacia, Bern, Switzerland) in DNA-binding buffer (10% glycerol, 50 mM HEPES, pH 7.5, 0.1 mM EDTA, 0.5 mM dithiothreitol, 100 mM NaCl) in a final volume of 10 µl. Competition experiments were performed by premixing the specific probe and competitor DNAs prior to the addition of cell extracts in DNA-binding buffer. Dissociation experiments were performed by incubating the probe and cell extract for 30 minutes to allow complex formation, followed by the addition of a 50-fold excess of unlabeled specific (site I, II or III) DNA as competitor. Incubation was continued for increasing lengths of time prior to electrophoresis. To correct for differences in the specific activities of the probes used in these experiments, extracts were incubated in the presence of equivalent nanograms of wild-type or mutant site I probe DNA in DNA-binding buffer. Equal amounts of radioactivity were then loaded on gels, and the complexes were separated by electrophoresis. Protein-DNA complexes were separated from free probe by electrophoresis at 25° C. in 6% or 6.5% polyacrylamide gels (37.5:1 acrylamide/bisacrylamide) prepared and run in 0.5×TBE (Tris-borate-EDTA) buffer (Maniatis et al., 1982, Molecular Cloning, A Laboratory Manual, Cold Spring Harbor, N.Y.).

RESULTS

Cellular proteins bind to sequences within oriS sites I, II and III.

Figure 2B:
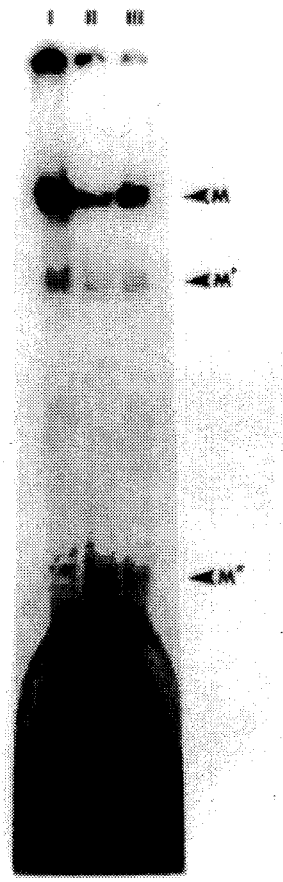

Gel shift analysis was used to study the interactions of cellular DNA binding proteins with HSV-1 oriS DNA sequences. Complex formation was assessed following incubation of uninfected cell extracts with site I DNA as well as with the highly homologous sites II and III DNAs (FIG. 2A). Incubation of uninfected Vero cell extracts with oriS site I DNA resulted in the formation of two protein-DNA complexes of different mobilities, complexes M and M' (FIG. 2B, lane 1). Three protein-DNA complexes were identified following incubation of uninfected cell extracts with the site II probe, two complexes with electrophoretic mobilities indistinguishable from complexes M and M', and a third complex, M", which exhibited a significantly faster electrophoretic mobility (FIG. 2B, lane 2). Three protein-DNA complexes with electrophoretic mobilities indistinguishable from complex M, M' and M" were also identified using the site III probe (FIG. 2B, lane III). Thus, proteins from uninfected cell extracts form complexes with three homologous but non-identical sequences in HSV-1 oriS, sites I, II and III.

Cellular factors bind specifically to oriS sequences.

To assess the specificity of the interactions between the cellular proteins and sites I, II and III DNAs, competition analysis was performed by incubation of uninfected cell extracts and radiolabeled site I, II, or III DNA probes in the presence of unlabeled homologous (site I, II, or III) DNA as competitor. Formation of the M-like complexes with site I, II, or III DNA decreased progressively with the addition of increasing concentrations of unlabeled homologous competitor DNA (FIG. 3A). As determined by interpolation of densitometric analysis, the protein components of the M-like complexes had higher affinity for site I and III DNAs as compared to site II DNA, which required a 3-fold higher concentration of homologous DNA to achieve 50% competition (FIG. 3B). The addition of 100-fold excess of non-specific DNA (NS-A or NF-I) had little effect on complex M formation with site I, II or III DNA (FIG. 3A). Therefore, formation of the cellular M-like complexes is the result of specific protein-DNA interactions between cellular protein(s) and site I, II and III DNA sequences, respectively.

Comparison of M-like complex interactions with site I DNA.

In addition to assessing the specificity of complex formation, competition experiments were performed to test the strength of the interactions between the cellular protein(s) in the M-like complexes with site I, II, and III DNA. In these experiments, uninfected cell extracts were incubated with radiolabeled site I, II, or III DNA in the presence of increasing concentrations of unlabeled site I DNA as competitor. The formation of the M-like complexes with radiolabeled site I, II, or III DNA was found to be reduced in the presence of excess unlabeled site I competitor DNA (FIG. 4) when interpolation of densitometric analysis was performed.

M-like complexes formed with site I, II, and III DNAs dissociate at similar rates.

The relative binding affinities of the protein(s) in the M-like complexes for sites I, II, and III DNAs were also assessed by dissociation rate analysis. In these experiments, uninfected cell extracts were incubated with radiolabeled site I, II, or III probe. Following an initial 30 minute incubation to allow complex formation, 50-fold excess of unlabeled homologous (site I, II, or III) DNA was added as competitor and incubation was continued for increasing lengths of time prior to electrophoresis. As shown in FIG. 5, the M-like complexes formed with site I, II, or III DNA dissociated to 50 to 60% of uncompeted levels within the first 2.5 minutes of incubation with competitor DNA, followed by a gradual decrease in complex formation that occurred at similar rates for each of the three DNAs. Therefore, cellular proteins dissociate from site I, II and III DNA at approximately equal rates.

Proteins from cell extracts of a variety of species bind specifically to site I DNA.

Cell extracts from a variety of species including human, monkey, rabbit, rat, mouse and hamster were tested in a gel shift assay for the presence of cellular proteins capable of specifically binding site I DNA. As shown in FIG. 6, cellular proteins capable of binding site I DNA sequences were present in every cell type tested (see lanes 1). Moreover, these protein-DNA complexes were only slightly reduced in the presence of 250-fold excess of unlabeled non-specific competitor DNA (NS-A; see lanes 2). However, the addition of 250-fold excess of unlabeled specific competitor DNA (site I) significantly decreased or totally eliminated complex formation (see lanes 3). Complex M' formation was also specifically competed in the presence of 250-fold excess of specific competitor DNA. Similarities in the mobilities of the complexes formed were most apparent among primate cell lines; the mobilities of complexes formed by extracts from the rabbit cell line (R3) were noticeably different from complexes formed with either the primate (Vero, HEL, HeLa) or rodent (LSH, PC12, C57/B16) cell extracts. In addition, the concentration of cellular site I binding proteins in each extract differed considerably. In FIG. 6, 10 μg of extract was incubated with site I DNA to demonstrate binding for two of the primate (Vero, monkey; HEL, Human) and the R3 (rabbit) cell lines. In contrast, 15 μg of extract was required to achieve the levels of binding shown in FIG. 6 with the rodent (LSH, hamster; PC12, rat; C57/B16, mouse) cell lines. Notably, 1 μg of extract was sufficient to achieve the elevated binding levels observed with the HeLa (human) cell extract. These results indicate that cellular site I binding proteins, or at least the DNA-binding domains of these proteins, are conserved to a considerable extent through evolution.

Protein-DNA complex formation with mutant forms of site I DNA defines the complex M protein binding site.

The experiments described above address the specificities and binding affinities of protein interactions with site I, II, and III DNA. In order to identify specific nucleotides within the site I sequence important for the formation of complex M, synthetic oligonucleotides having sequences based upon that of site I, but containing specific mutations in site I were used as probes (FIG. 7). The results of these experiments (FIGS. 8A and B) indicate that the formation of complex M is unaffected by the specific dinucleotide deletions in probes 1, 2, 3, and 8. The mutations contained in these probes eliminate nucleotides located near the 5' end of the site I sequence (probes 1, 2, 3) or delete a TT dinucleotide near the center of the site I sequence (probe 8). The formation of complex M was significantly enhanced as compared to wild type by the mutations in probes 12 (300% of wild type) and 13 (160% of wild type), which probes contain single or double nucleotide transversions in the center of the site I sequence (FIG. 7). Complex M formation was decreased by over 70% by the mutation in probe 4 in which only a single G residue was deleted. In addition, complex formation was reduced by 77–82% relative to wild type with mutant probes 5, 6, 7, 9, 10 and 11. Complex M formation was also reduced by 90% with a probe containing a trinucleotide deletion that specifically eliminates the TCC residues at the 3'-end of the site I sequence (FIG. 1). These results define a binding site, 5'-GTTCGCACTTGCTCCCAAT-3' [SEQ ID NO:49], within site I DNA for the cellular protein present in complex M. This protein is named origin factor 1, or OF-I.

The CP2 binding site competes with site I for OF-I binding.

Figure 9A:
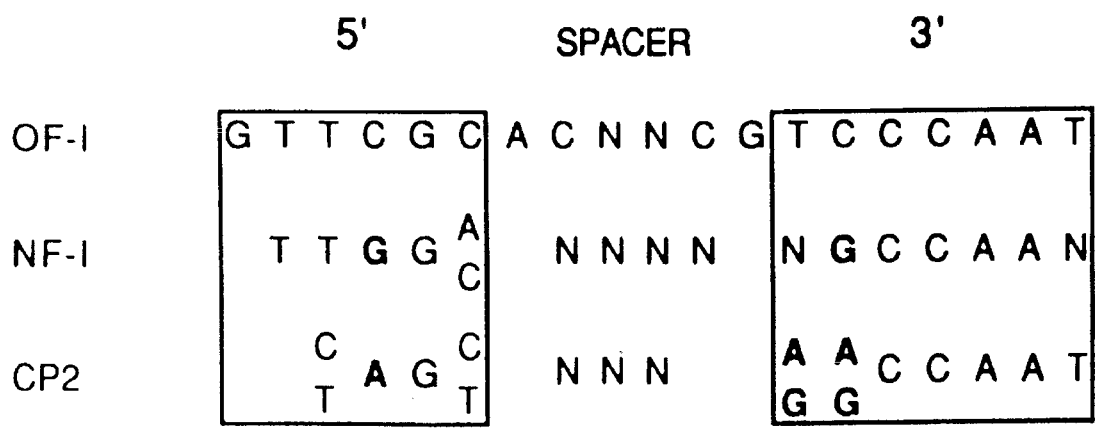

The OF-I binding site within site I DNA, defined above, exhibits significant homology to previously identified binding sites for the cellular CCAAT family of DNA binding proteins. The CCAAT factor NF-I has been shown to enhance initiation of DNA replication in adenoviruses and JC virus (Challberg et al., 1989, Ann. Rev. Biochem. 58:671; Sock et al., 1991, Virology 182:298). The consensus NF-I binding site (Jones et al., 1987, Cell 48:79) differs from the OF-I site by two nucleotides and the length of the spacer region (FIG. 9A). The consensus binding site of the CCAAT factor CP2 (Chodosh et al., 1988, Cell 53:11) differs from the OF-I site by three nucleotides as well as the length of the spacer, while the CP2 binding site within the upstream region (−81 to −68) of the H-2K$^b$ promoter differs by only one nucleotide and the spacer region (Chodosh et al., 1988, Cell 53:11).

Figure 9B:
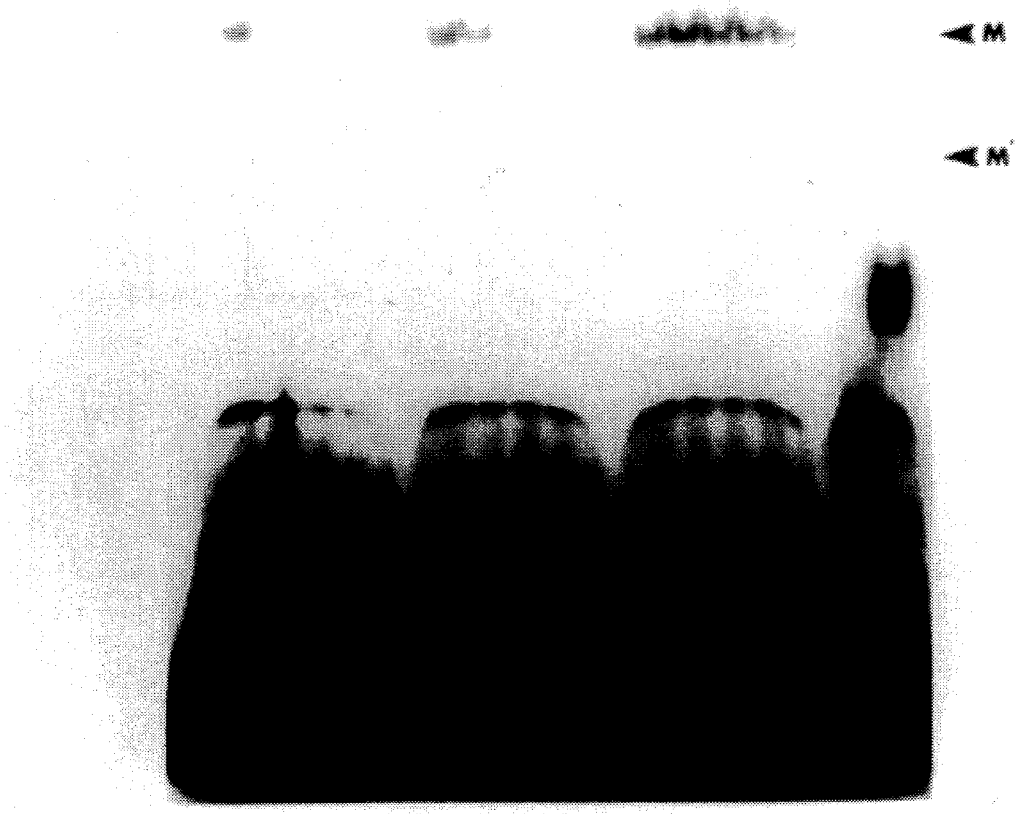

In order to compare the relative binding specificities of OF-I and CCAAT binding proteins with site I DNA, uninfected cell extracts were incubated with radiolabeled site I DNA in the presence of increasing concentrations of unlabeled DNA containing site I, NF-I or CP2 H-2K$^b$ (−81 to −68) binding sites as competitors (FIG. 9B). The addition of increasing amounts of the NF-I binding site oligonucleotide had little effect on OF-I binding to site I DNA even when present in concentrations up to 100-fold of site I probe DNA; OF-I binding was reduced 2-fold in the presence of 200-fold excess of NF-I DNA. Both the site I OF-I-binding and the CP2-binding oligonucleotides competed effectively with radiolabeled site I DNA for OF-I binding, although the CP2 oligonucleotide competed less effectively than did site I DNA. Complex formation between (a) proteins in uninfected cell extracts and (b) radiolabeled CP2 or NF-I binding sites was also tested. Complexes with mobilities similar to complexes M and M' were apparent following incubation with the CP2 oligonucleotide, while a complex of significantly greater mobility was apparent with the NF-I oligonucleotide. Taken together, these results demonstrate that OF-I binds to sequences within the HSV-1 origin of replication at oriS and indicate that OF-I is likely to be a member of the CCAAT family of DNA binding proteins.

Comparison of origin structure and site I DNA homology among herpesviruses.

The various origins of replication of HSV-1, HSV-2, MDV, EHV-1 and VZV are compared in FIG. 10A, with respect to site I, II and II DNA. Sites II and III are conserved in HSV-1 and HSV-2, whereas homology only to site I is evident in MDV, EHV-1 and VZV. Furthermore, the origins of replication of MDV and EHV-1 each contain sequences homologous to site I on both sides of the AT-rich region, which is structurally similar to oriL of both HSV-1 and HSV-2. VZV has an additional sequence, 50 bp upstream form site I, which shares 62% homology with site I of HSV-1 oriS across the 21 bp sequence shown in FIG. 10B.

A CTAAT motif is present in the oriS site II and oriL site I elements of HSV-1 and HSV-2 as well as in the oriS site I in HSV-1 (FIG. 10B). A CCAAT motif is conserved in the oriS site I of HSV-1 and in regions of the EHV-1 and MDV origins of replication that share homology with HSV-1 site I. Conservation of these motifs suggests that they are functionally significant.

Effect of mutations on HSV-1 DNA replication.

To test the effects of various mutations in the oriS sequence on HSV-1 DNA replication, the following experiments were performed. Mutations were introduced into either the OBP or OF-I binding sites of oriS by site-specific mutagenesis of plasmid DNA containing 1715 nucleotides of sequences flanking and including oriS. The mutations and the results of the experiments are shown in FIG. 11. Mutant T contained a mutation (CA to GG) in the OF-I binding site of site I; mutant R contained a mutation (C to A) in both the OF-I and OBP binding sites in site I; and, mutant O contained a mutation (CT to AA) in the OBP and OF-I binding sites in site III. The effect of the mutations on DNA replication was tested by transfecting Vero cells with 10 µg of either wild type or mutant oriS-containing plasmids. At 16 to 20 hours post-transfection, transfected cells were superinfected with 10 PFU of HSV-1 per cell. DNA was extracted from the cells following an additional 18 hours of incubation, and the ability of wild type virus to stimulate replication of the transfected plasmids was assessed as described by Wong et al. (1991, J. Virol. 65:2601). Briefly, 5 µg of DNA were digested with DpnI and EcoRI, and the restricted DNA was electrophoresed and examined in a Southern blot using radiolabelled pUC19 (vector) DNA as a probe. The level of replication of the plasmid containing wild type oriS sequences was considered to be 100% and the level of replication of the mutant-containing plasmids was then assessed relative to this value.

Mutant T was found to replicate at a level that was 57% of the wild type level, while mutant R replicated to only 8% of the wild type level. These results indicate the relative importance of the OF-I and overlapping OF-I and OBP binding sites in site I of oriS. The mutations introduced into the OF-I and OBP binding sites in site III resulted in a replication level of 332% of the level of the wild type site III DNA, suggesting that these particular mutations enhance binding of at least one of these proteins. This was confirmed by the finding that, when examined in gel shift assays, protein binding to a DNA sequence containing a mutation in site I comparable to that in mutant O resulted in a significant enhancement of binding of OF-I to this DNA (probe 13, FIGS. 8A and B), while binding of OBP was diminished.

Purification of OF-I.

Purification of OF-I can be performed essentially as described by Chodosh et al. (1988, Cell 53:11) and Samuels et al. (1982, J. Biol. Chem. 257:14419), wherein the purification of CP2 is described. However, other biochemical techniques common in the art may also be used. To determine whether OF-I and CP2 have the same binding properties, gel shift assays can be performed in parallel with the purification procedure, using two probes of identical length which contain either HSV-1 oriS site I DNA or rat γ-fibrinogen (γ-FBG) promoter to which either OF-I (described above) or CP2 (Chodosh et al., 1988, Cell 53:11; Samuels et al., 1982, J. Biol. Chem. 257:14419) binds.

The essential details of one purification procedure are as follows: HeLa cells grown in suspension at 37° C. to a final cell density of approximately $8 \times 10^5$ cells/ml are harvested by centrifugation at 3000×g for 5 min. Whole cell extracts can be prepared from these cells using the method of Manley et al. (1980, Proc. Natl. Acad. Sci. USA 77:3755). Extracts are dialyzed against buffer B (20 mM HEPES pH 7.9, 17% glycerol, 1 mM DTT, 1 mM EDTA, 12.5 mM $MgCl_2$)+0.1M KCl, centrifuged at 10,000×g for 20 min and then are dialyzed again against buffer A (20 mM HEPES pH 7.9, 20% glycerol, 1 mM DTT, 1 mM EDTA)+0.1M KCl. Extracts can be frozen in liquid nitrogen and stored at 80° C. until a sufficient number of cells, approximately $5 \times 10^{10}$, have been harvested in this manner Next, phosphocellulose chromatography is performed. Phosphocellulose (Whatman) is washed in buffer A+0.1M KCl 0.2 mg/ml bovine serum albumin (BSA) and in buffer A+0.1M KCl. It is then equilibrated with buffer A+0.04M KCl. Whole cell extracts are thawed on ice, adjusted to 0.04M KCl, and loaded onto a column containing the treated phosphocellulose (8 mg protein/ml bed volume). The column is then washed with buffer A+0.04M KCl (fraction A) and bound proteins are eluted in a step-wise fashion with 0.35M KCl, 0.6M KCl, and 1.0M KCl+0.2 mg/ml BSA in buffer A, giving rise to fractions B, C, and D, respectively. Each of these fractions is dialyzed individually against buffer A+0.1M KCl, quick-frozen, and stored at −80° C.

The CP2 protein, as well as other CCAAT binding factors such as CP1 and NF-I, have been shown to be heterodimeric DNA binding proteins. If this also proves to be the case for OF-I, further purification of each subunit will require chromatography of two separate phosphocellulose fractions. An example of how this can be accomplished is provided below.

Phosphocellulose fraction A (the 0.04M KCl flowthrough fraction) is adjusted to 0.15M KCl and loaded onto a pre-equilibrated DEAE-Sephacel (Pharmacia) column (equilibrated in buffer A+0.15M KCl (8.5 mg protein/ml bed volume). The column is then washed with buffer A+0.15M KCl (flow through) and proteins are eluted in a step-wise fashion with 0.35M and 1M KCl in buffer A. Fractions that are collected (fractions AA, AB, AC, respectively) are dialyzed against buffer A+0.1M KCl, quick-frozen, and stored at −80° C.

In the next step of the procedure, dialyzed phosphocellulose fraction C (0.6M KCl fraction) is adjusted to 5 mM $MgCl_2$ and applied to a DNA-cellulose (Sigma) column (2 mg protein/ml bed volume) which was washed and pre-equilibrated in buffer C (20 mM HEPES pH 7.9, 20% glycerol, 1 mM DTT, 1 mM EDTA, 5 mM $MgCl_2$)+0.1M KCl. The column is then washed with buffer C+0.1M KCl and proteins are eluted in a step-wise fashion with 0.3M KCl, 0.6M KCl, and 1M KCl in buffer C. Fractions CA, CB, CC, CD, which are collected can be dialyzed against buffer A+0.1M KCl, quick-frozen, and stored at −80° C.

In order to obtain a highly purified preparation of OF-I, chromatography through a site I DNA-affinity column can be performed. The procedure for affinity purification can be performed essentially as described for purification of the CCAAT protein, C1 (Chodosh et al., 1988, Cell 53:11). An example of such a procedure is described below.

A site I-containing oligonucleotide of approximately 32 base pairs can be biotinylated with biotin-11-dUTP (Bethesda Research Laboratories (BRL)) in the presence of the Klenow fragment of E. coli DNA polymerase I and the appropriate nucleotides. The probe is then incubated at room temperature for 30 minutes with poly (dI-dC). poly (dI-dC), BSA, and fractions AB and CB in binding buffer (50 mM HEPES pH 7.5, 10% glycerol, 0.5 mM DTT, 0.1 mM EDTA, 100 mM NaCl). Streptavidin (BRL) is then added and the incubation is continued for an additional 15 minutes. The reactions are then chilled on ice, added to pre-equilibrated biotin-cellulose (Pierce), and the suspension is mixed at 4° C. for 30 min. The suspension is then-centrifuged, the pellet is washed with cold binding buffer, and proteins are eluted in a step-wise fashion from a mini-column with 0.35M KCl, 0.6M KCl, and 1.0M KCl in buffer A+BSA. Fractions are collected and dialyzed against buffer A+0.06M KCl.

The gel-shift assay can be used to monitor binding of proteins to site I and γ-FBG DNAs as described above. Briefly, radiolabeled site I DNA (1–2 ng; $3–5 \times 10^4$ cpm) can be incubated with HeLa cell extract (1 µg) or fractionated extract in binding buffer for 30 minutes, followed by electrophoresis of the complexes through polyacrylamide gels. The yield of proteins at each step in the purification procedure can be determined using the method of Bradford (1976, Anal. Biochem. 72:248).

Characterization of OF-I during purification.

During the purification procedure, OF-I and CP2 can be compared with regard to their chromatographic properties, methylation interference patterns and competition binding assays in gel shift experiments. In addition, each of the fractions obtained above that contain OF-I activity can be examined by SDS-PAGE and by silver staining in order to determine the number and apparent molecular weight of the polypeptide(s) that comprise OF-I, and to assess the purity of the preparation.

To examine the DNA binding activity of individual polypeptide species that are contained within fractions in the final purification step, the polypeptide can be electrophoresed through polyacrylamide, eluted, renatured (Hager at al., 1980, Anal. Biochem. 109:76) and assayed individually for DNA binding activity using the oriS probes described above.

Preparation of antibodies to OF-I.

Polyclonal antibodies can be generated directed against gel-purified OF-I as described for other transcription factors (Jones et al., 1987, Cell 48:79; Pruijn et al., 1989, Nucl. Acids Res. 15:1845), provided OF-I can be purified in relatively abundant quantities. Affinity purification of HeLa cell transcription factors have, in general, resulted in approximately 1,000 to 100,000-fold purification, with a yield of 10 µg–100 µg of purified protein from 1–2×10$^{10}$ cells (Jones et al., 1987 Cell 48:79; Huang et al., 1990, Genes and Dev. 4:287; O'Neill et al., 1988, J. Biol. Chem. 263:931; Chodosh et al., 1986, Mol. Cell. Biol. 6:4723). It is anticipated that 2–3 rounds of affinity purification of OF-I from 5×10$^{10}$ HeLa cells will be required to obtain sufficient protein (i.e., at least 50–100 µg of protein) for the generation of polyclonal antibodies.

Affinity-purified OF-I (200 µg) is first injected into rabbit lymph nodes followed by subcutaneous booster inoculations at regular intervals (Jones et al., 1987, Cell 48:79). Both preimmune serum and serum obtained after each booster injection can be assayed for activity against OF-I in crude cellular extracts and in affinity purified fractions. This analysis can be performed by gel-shift assay as follows. Radiolabelled site I DNA is incubated in the presence of an OF-I-containing preparation and either preimmune or immune serum. The disappearance of cellular complex M and the subsequent appearance of a band which migrates more slowly in the presence of OF-I antiserum is indicative that the antigen and antibody specifically interact with each other. In addition, protein DNA complexes can be detected by immunoprecipitation (Jones et al., 1987, Cell 48:79).

Alternatively, purified OF-I can be microsequenced (Tempst et al., 1990, Electrophoresis 11:537), peptides can be generated using standard technology available in the art, and antibodies can be obtained which are directed against specific peptides (Harlow et al., 1988, In: Antibodies, A Laboratory Manual, Cold Spring Harbor, N.Y.).

Monoclonal antibodies directed against OF-I, or fragments thereof, can be generated using standard hybridoma technology available in the art.

Cloning of the gene encoding OF-I.

The gene encoding OF-I can be cloned by any of a number of different procedures available in the art which are described, for example, in Sambrook et al. (1989, Molecular Cloning, A Laboratory Manual, Cold Spring Harbor, N.Y.).

Two examples of cloning procedures are provided below. Oligonucleotides which code for stretches of 10–20 amino acids of OF-I (determined by microsequencing of the affinity purified protein as described above) can be synthesized on an oligonucleotide synthesizer. Since human cells express OF-I (see FIG. 6), these oligonucleotides can be used as hybridization probes to screen a human cDNA library. Positive clones can be sequenced and the amino acid sequence deduced from the nucleotide sequence can be compared with the sequence of the purified protein. Alternatively, anti-OF-I antibody can be used to screen a human cDNA expression library for the presence of peptides and proteins that react with the antibody. Positive clones can then be isolated, sequenced and characterized as described above.

Further characterization of OF-I.

OF-I can be characterized further with regard to its ability to bind to origin specific vital DNA sequences, OBP or both viral DNA and OBP as described below.

Binding of OF-I to origin specific viral DNA sequences can be assayed using the methods described above, or by performing Southwestern analysis, which is now described. Uninfected cell extracts or purified OF-I is electrophoresed through SDS-polyacrylamide gels and transferred to a support membrane using standard western blotting techniques which are described, for example, in Sambrook et al. (Supra). The membrane is incubated in the presence of radiolabelled probes comprising oriS sequences specifying site I, II or III sequences, or mutants thereof, following the general methods described in Michael et al. (1988, Science 239:1531). After incubation, the membrane is washed to remove any unbound label, dried and then exposed to X-ray film.

The interaction between OF-I and OBP can be characterized using standard biochemical techniques or by using Far Western analysis. If the latter technique is used, it is first necessary to obtain OF-I or OBP in purified form. Methods for the purification of OF-I are described above and methods for the purification of OBP are described in (Koff et al., 1988, J. Virol. 62:4096). In addition, large quantities of either protein can be obtained using any ordinary expression system available for the expression of such proteins described, for example, in Sambrook et al. (Supra). The gene encoding either OBP or OF-I can be cloned under the expression of either a eukaryotic or a prokaryotic promoter that is capable of driving high levels of expression of the protein products in either eukaryotic or prokaryotic cells. Alternatively, the genes encoding either protein can be expressed in vitro by cloning the coding sequences into, for example, a pGEM vector (Promega), wherein RNA can be transcribed from such a vector in vitro by adding the appropriate prokaryotic RNA polymerase and reagents and buffers. Relatively large quantities of protein can be obtained by translation of this RNA in vitro in a rabbit reticulocyte or wheat germ system. Such technology is well known to any ordinary molecular biologist and is described in many manuals of molecular biology including Sambrook et al. (Supra). Since OBP has been cloned, sequenced and purified, antibodies to this protein can be generated by any standard method described, for example, in Harlow et al. (Supra), as described above.

Fragments of peptides of either protein can also be obtained in relatively large quantities by cloning fragments of the respective genes into the expression plasmids described above. Expression of such genes in these expression systems will result in the production of fragments of proteins.

Far Western analysis, which is now described, is one method that can be used to examine the interaction between OBP and OF-I. Proteins contained within uninfected cell extracts, or purified OF-I, are electrophoresed on SDS-polyacrylamide gels and are subsequently transferred to a support membrane. The membrane is reacted with in vitro synthesized OBP or fragments thereof, synthesized in the presence of a radioactive label such that the polypeptide incorporates the label during the synthesis. The conditions under which the proteins on the membrane are incubated are those that will promote binding of OBP to OF-I similar to binding that occurs in an intact cell. The procedures, and several modifications thereof for Far Western analysis are described in detail in Lee et al. (991, Cell 67:365), Horikoshi et al. (Proc. Natl. Acad. Sci. USA 88:5124) and Homann et al. (1991, J. Virol. 65:1304). At the end of the incubation period, the membrane is washed and the position of any complexes and the amount of OBP (or a fragment of OBP) that is bound to OF-I on the membrane is assessed by autoradiography.

One method for identifying the amino acids of OBP that are required for binding to OF-I involves the use of assays utilizing a variety of individual fragments of OBP. Generation of such fragments is easily accomplished by subcloning fragments of the gene encoding OBP into an expression system, such as that described above, and then expressing the protein products from these fragments. Fragments that bind in the assay will contain amino acids required for binding, whereas fragments that do not bind are unlikely to contain such amino acids. The amino acids of OF-I that are required for its binding to OBP can be identified exactly as described above, except that OBP is electrophoresed on the gel and radiolabelled OF-I, or fragments thereof, are reacted with membrane-immobilized OBP.

A second method for identifying the amino acids of OBP and OF-I required for their interaction involves the use of DNA affinity columns as described above. Uninfected cell extracts (or purified OF-I) and OBP are loaded onto the column. The column is then washed and the DNA-binding proteins are eluted in the presence of salt. The eluate can be treated with reversible bivalent cross-linking reagents of increasing length (6 to 16 Angstroms) as described in Pascal et al. (1991, Genes and Dev. 5:1646). The reaction product is subjected to limited protease cleavage (Pascal et al., Supra). Cross-linked peptides are separated from unlinked peptides by high performance liquid chromatography (HPLC) using standard procedures, and the cross-link is reversed. The peptides are separated by SDS-PAGE, transferred to a membrane and are subjected to microsequencing so that the precise amino acids responsible for binding of one protein to another can be identified. Reaction mixtures can include each of a variety of combinations of fragments of OBP incubated with whole OF-I in the presence of DNA, and each of a variety of combinations of fragments of OF-I incubated with whole OBP in the presence of DNA. Alternatively, fragments that are shown to bind to each other using the methods described above can be used to further determine the precise amino acids that are required for binding.

A third method for identifying the amino acids of OBP and OF-I required for their interaction involves the use of immunoprecipitation. For example, uninfected cell extracts (or purified OF-I can be incubated together as described above. Antibody to either OF-I or OBP is added to the incubation mixture to precipitate complexes containing either protein. The antibody is removed from the complexes by standard procedures and the amino acids of either protein that are bound to each other are determined in cross-linking experiments as described above.

Alternative methods for examining protein-protein and protein-DNA interactions between OBP, OF-I and DNA include the following. Bacterial cells capable of expressing OBP or fragments thereof as fusion proteins with glutathione-S-transferase, are lysed by mechanical means, such as sonication or French press. The proteins so released are incubated with prewashed glutathionine-Sepharose beads such that the proteins bind to the beads. Radioactively labelled uninfected eukaryotic cell extracts are then incubated with the beads in the presence or absence of oriS sequences. At the end of the incubation period, proteins and/or DNA bound to the beads are subjected to limited protease cleavage and separated from unbound components by centrifugation and subsequent washing. The mixture is then boiled and the products are analyzed by SDS-polyacrylamide gel electrophoresis. The technology described is standard in the art and can be found, for example, in Current Protocols in Molecular Biology (Supra).

USE OF THE INVENTION

The compositions and methods of the invention can be used to treat viral diseases of mammals. They can also be used to identify additional compounds that might be useful as therapeutics for viral diseases. While the examples given above are directed to HSV-1 replication and the proteins required for such replication, the compositions and methods of the invention are not limited to this virus. Other members of the herpesvirus family and other DNA-containing viruses also specify proteins which bind to specific viral DNA sequences in the presence of cellular proteins in order to facilitate virus replication. Many of these proteins and the sequences to which they bind are known in the art, and others can be identified using the methods and teaching described above for HSV-1.

Oligonucleotides to which OF-I and OBP or OF-I-like and OBP-like proteins bind may be used to disrupt virus replication in infected cells by binding to either protein, thereby inhibiting binding of that protein to identical DNA sequences in the viral genome. Since the natural function of these proteins when bound to the viral genome is to promote virus replication, disruption of this binding will serve to inhibit virus replication. In a similar manner, peptides or antibodies capable of binding to OBP, OF-I, or OBP-like or OF-I-like sequences are useful for disrupting the interaction of OBP with OF-I. Peptides or antibodies capable of binding to OF-I or OBP can be used to disrupt the interaction of either of these proteins with the DNA sequences to which they bind, which would also result in inhibition of virus replication.

Oligonucleotides that can be used in the methods of the invention include those which specify the binding site for OBP, OF-I or proteins with similar properties that are encoded by other viruses and/or cells, or they may be those which bind to these proteins with an even higher affinity than that of wild type sequences. Peptides that can be used in the methods of the invention are those that contain an amino acid sequence contained within OBP or OF-I, and which is required for binding or the interaction of (i) OBP to OF-I; (ii) OF-I to OBP; (iii) OF-I to DNA; (iv) OBP to DNA; or, (v) OBP and OF-I to DNA. The identification of such peptides is described in detail above. Antibodies directed against the protein-protein or protein-DNA binding regions of OF-I or OBP (or OF-I-like and OBP-like proteins) are also useful in the invention and can be used in the methods of the invention in a manner similar to that described for the peptides of the invention.

A simple cell culture assay can be used to determine whether such oligonucleotides, peptides and antibodies are capable of inhibiting replication of a virus. Alternatively, in vitro assays such as gel-shift assays, affinity chromatography etc., (described above) can also be used to examine the effect of compounds on complex formation. A compound determined to have an effect on complex formation is a candidate antiviral compound potentially capable of disrupting virus replication. The invention is also useful for the identification of other compounds (other peptides and non-peptides) that are potential inhibitors of virus replication. One example of how this is accomplished involves incubation of OF-I, OBP in the presence or absence of a DNA sequence to which these proteins bind, and in the presence of a candidate inhibitor of complex formation. Compounds that inhibit complex formation are potential HSV-1 antiviral agents.

In a cell culture assay, the oligonucleotide, peptide or antibody is added to a culture of cells in a formulation that permits entry of the compound into the cell. Transfection of cells with nucleic acid sequences is common in the art and methods of transfection are described in Sambrook et al. (Supra) and in Current Protocols in Molecular Biology (Supra). Similarly, proteins and peptides can be added to cells using the technique of scrape-loading (Fechheimer et al., 1987, Proc. Natl. Acad. Sci. USA 84:8463) or alternatively, certain proteins or peptides can be taken up by cells directly (Frankel et al., 1988, Cell 55:1189; Green et al., 1988, Cell 55:1179; Meek et al., 1990, Nature 343:90). The oligonucleotides and peptides can be added to the cells either before or after the cells are infected with the appropriate virus. The effect of the compounds on virus replication can be assessed in a conventional plaque or burst assay, by immunofluorescent techniques, or by assaying for viral DNA replication. Compounds that inhibit virus replication can then be tested for their ability to inhibit virus replication and pathogenesis, and tested for toxicity in animal models according to standard methods.

The ability of compounds to inhibit virus replication can be determined in any of the assays described above for peptides, antibodies or oligonucleotides. Compounds that have the potential to inhibit the replication of other DNA containing viruses can be screened in a similar manner by simply including the appropriate proteins and oligonucleotides, determined as described herein, in the reaction mixture. The screening assay can also be performed in the absence of the DNA sequences in that compounds may also be screened for their ability to disrupt binding of OF-I (or OF-I-like proteins) directly to OBP (or OBP-like proteins) using the assays described above.

Oligonucleotides, peptides and antibodies of the invention that inhibit virus replication may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema). The compounds can be administered to the mammal in a dosage of 0.1 µg/kg/day to 5 mg/kd/day, either daily or at intervals sufficient to inhibit virus replication and alleviate the symptoms of the disease. Precise formulations and dosages may be determined using standard techniques, by a pharmacologist of ordinary skill in the art.

Screening assays such as those described above can be incorporated into a kit. The kit might comprise OF-I, OBP and/or a DNA sequence, a means for identifying the formation of complexes and instructions for using the kit.

We claim:

1. A method of screening a candidate compound for antiviral activity, said method comprising combining in the presence or absence of a candidate compound a DNA comprising a herpesvirus origin of DNA replication and a cell extract comprising a cellular protein capable of binding to SEQ ID NO:49 under conditions sufficient to form an M-like complex, provided that said cellular protein is not a DNA polymerase; and determining whether the level of formation of said M-like complex is lower in the presence of said candidate compound than in the absence of said candidate compound, a lower level in the presence of said candidate compound being an indication that said candidate compound possesses antiviral activity.

2. The method of claim 1, wherein said herpesvirus is selected from the group consisting of herpes simplex virus type 1, herpes simplex virus type 2, varicella zoster virus, equine herpes virus type 1 and Marek's disease virus.

* * * * *